(12) United States Patent
Bhatnagar et al.

(10) Patent No.: US 8,679,166 B2
(45) Date of Patent: Mar. 25, 2014

(54) PROSTHESIS WITH A SELECTIVELY APPLIED BONE GROWTH PROMOTING AGENT

(75) Inventors: Mohit K. Bhatnagar, Potomac, MD (US); Jack Y. Yeh, North Potomac, MD (US); Sudarshana Sona Bhatnagar, legal representative, Potomac, MD (US)

(73) Assignee: JMEA Corporation, Rockville, MD (US)

( * ) Notice: Subject to any disclaimer, the term of this patent is extended or adjusted under 35 U.S.C. 154(b) by 0 days.

(21) Appl. No.: 13/548,612

(22) Filed: Jul. 13, 2012

(65) Prior Publication Data

US 2012/0277804 A1 Nov. 1, 2012

Related U.S. Application Data

(62) Division of application No. 11/740,181, filed on Apr. 25, 2007, now Pat. No. 8,241,357.

(51) Int. Cl.
*A61B 17/80* (2006.01)

(52) U.S. Cl.
USPC .............................. 606/298; 606/280; 606/70

(58) Field of Classification Search
USPC .............................. 606/246, 280–299, 70, 71
See application file for complete search history.

(56) References Cited

U.S. PATENT DOCUMENTS

| | | | |
|---|---|---|---|
| 3,605,123 A | 9/1971 | Hahn | |
| 4,177,524 A | 12/1979 | Grell et al. | |
| 4,714,469 A | 12/1987 | Kenna | |
| 4,834,757 A | 5/1989 | Brantigan | |
| 5,098,434 A | 3/1992 | Serbousek | |
| 5,190,545 A | 3/1993 | Corsi et al. | |
| 5,306,275 A | 4/1994 | Bryan | |
| 5,348,026 A | 9/1994 | Davidson | |
| 5,360,448 A | 11/1994 | Thramann | |
| 5,405,389 A | 4/1995 | Conta et al. | |
| 5,505,736 A | 4/1996 | Reimeis et al. | |
| 5,545,165 A | 8/1996 | Biedermann et al. | |
| 5,571,139 A | 11/1996 | Jenkins, Jr. | |
| 5,785,710 A | 7/1998 | Michelson | |
| 6,206,924 B1 | 3/2001 | Timm | |
| 6,264,656 B1 | 7/2001 | Michelson | |
| 6,277,120 B1 | 8/2001 | Lawson | |
| 6,605,089 B1 | 8/2003 | Michelson | |

(Continued)

FOREIGN PATENT DOCUMENTS

| | | |
|---|---|---|
| EP | 0532421 | 3/1993 |
| JP | 2209148 | 8/1990 |

(Continued)

OTHER PUBLICATIONS

Office Action mailed Mar. 10, 2010 in U.S. Appl. No. 11/840,707.

(Continued)

*Primary Examiner* — Mary Hoffman
*Assistant Examiner* — Christina Negrellirodriguez
(74) *Attorney, Agent, or Firm* — Plumsea Law Group, LLC

(57) ABSTRACT

An implantable prosthesis system including a selectively applied bone growth promoting agent is disclosed. The types of prostheses which may include a selectively applied bone growth promoting agent include rods, fracture plates, screws, as well as other types of prostheses. Additionally, the structural composition of many types of prostheses may be modified to help induce bone ingrowth and allow for fusion with the implantable prosthesis.

21 Claims, 16 Drawing Sheets

(56) References Cited

U.S. PATENT DOCUMENTS

| | | | |
|---|---|---|---|
| 6,790,233 B2 | 9/2004 | Brodke et al. | |
| 7,074,221 B2* | 7/2006 | Michelson | 606/70 |
| 7,281,925 B2 | 10/2007 | Hall | |
| 2002/0138144 A1 | 9/2002 | Michelson | |
| 2002/0173850 A1 | 11/2002 | Brodke et al. | |
| 2004/0034351 A1 | 2/2004 | Sherman et al. | |
| 2004/0087950 A1 | 5/2004 | Teitelbaum | |
| 2004/0215341 A1 | 10/2004 | Sybert et al. | |
| 2004/0225360 A1 | 11/2004 | Malone | |
| 2004/0253185 A1 | 12/2004 | Herweck et al. | |
| 2005/0004573 A1 | 1/2005 | Abdou | |
| 2005/0015088 A1 | 1/2005 | Ringeisen | |
| 2005/0015154 A1 | 1/2005 | Lindsey et al. | |
| 2005/0038512 A1 | 2/2005 | Michelson | |
| 2005/0065604 A1 | 3/2005 | Stoll | |
| 2005/0075645 A1 | 4/2005 | Eckman | |
| 2005/0090822 A1 | 4/2005 | DiPoto | |
| 2005/0187555 A1 | 8/2005 | Biedermann et al. | |
| 2005/0187626 A1 | 8/2005 | McKay et al. | |
| 2006/0036322 A1 | 2/2006 | Reiley | |
| 2006/0041259 A1 | 2/2006 | Paul et al. | |
| 2006/0041262 A1 | 2/2006 | Calvert et al. | |
| 2006/0085009 A1 | 4/2006 | Truckai et al. | |
| 2006/0093646 A1 | 5/2006 | Cima et al. | |
| 2006/0111715 A1 | 5/2006 | Jackson | |
| 2006/0149255 A1 | 7/2006 | Doubler et al. | |
| 2006/0173542 A1 | 8/2006 | Shikinami | |
| 2006/0190080 A1 | 8/2006 | Danoff et al. | |
| 2006/0229615 A1 | 10/2006 | Abdou | |
| 2006/0241623 A1 | 10/2006 | Lim et al. | |
| 2006/0241776 A1 | 10/2006 | Brown et al. | |
| 2006/0264948 A1 | 11/2006 | Williams | |
| 2006/0264950 A1 | 11/2006 | Nelson et al. | |
| 2006/0276788 A1 | 12/2006 | Berry et al. | |
| 2007/0055373 A1 | 3/2007 | Hudgins et al. | |
| 2007/0083265 A1 | 4/2007 | Malone | |
| 2007/0173938 A1 | 7/2007 | Sweeney | |
| 2007/0179599 A1 | 8/2007 | Brodbeck et al. | |
| 2007/0233071 A1 | 10/2007 | Dewey et al. | |
| 2007/0270812 A1* | 11/2007 | Peckham | 606/61 |
| 2007/0270821 A1 | 11/2007 | Trieu et al. | |
| 2007/0270858 A1 | 11/2007 | Trieu et al. | |
| 2008/0154378 A1 | 6/2008 | Pelo | |
| 2008/0161927 A1* | 7/2008 | Savage et al. | 623/17.16 |
| 2008/0269893 A1 | 10/2008 | Bhatnagar et al. | |
| 2010/0168841 A1 | 7/2010 | Furst et al. | |

FOREIGN PATENT DOCUMENTS

| | | |
|---|---|---|
| JP | 7275268 | 10/1995 |
| WO | 2008134411 | 11/2008 |
| WO | 2009025884 | 2/2009 |

OTHER PUBLICATIONS

Response to Office Action filed Jun. 10, 2010 in U.S. Appl. No. 11/840,707.
Interview Summary mailed Jul. 6, 2010 in U.S. Appl. No. 11/840,707.
Final Office Action mailed Sep. 21, 2010 in U.S. Appl. No. 11/840,707.
Interview Summary mailed Feb. 18, 2011 in U.S. Appl. No. 11/840,707.
Request for Continued Examination filed Feb. 18, 2011 in U.S. Appl. No. 11/840,707.
Response filed Feb. 18, 2011 in U.S. Appl. No. 11/840,707.
International Search Report and Written Opinion, mailed Jun. 4, 2009, from PCT Application No. PCT/US2008/061408.
International Search Report and Written Opinion, mailed Jun. 4, 2009, from PCT Application No. PCT/US2008/061397.
Office Action mailed May 19, 2009 in U.S. Appl. No. 11/859,386.
Response to Office Action filed Jun. 17, 2009 in U.S. Appl. No. 11/859,386.
Office Action mailed Aug. 10, 2009 in U.S. Appl. No. 11/859,386.
Response to Office Action filed Nov. 9, 2009 in U.S. Appl. No. 11/859,386.
Interview Summary mailed Nov. 23, 2009 in U.S. Appl. No. 11/859,386.
Office Action mailed Jan. 12, 2010 in U.S. Appl. No. 11/859,386.
Response to Election of Species Requirement filed Feb. 9, 2010 in U.S. Appl. No. 11/859,386.
Final Office Action mailed May 7, 2010 in U.S. Appl. No. 11/859,386.
Interview Summary mailed Oct. 1, 2010 in U.S. Appl. No. 11/859,386.
Request for Continued Examination filed Oct. 6, 2010 in U.S. Appl. No. 11/859,386.
Response filed Oct. 6, 2010 in U.S. Appl. No. 11/859,386.

* cited by examiner

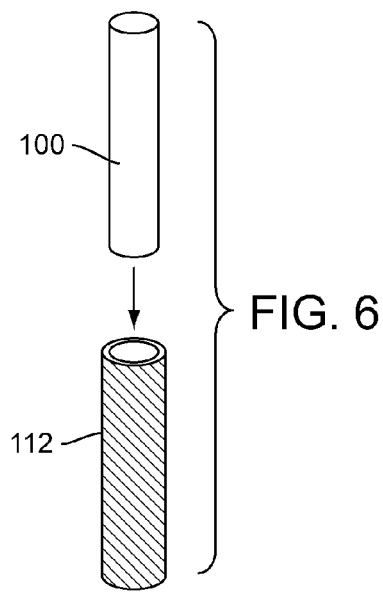
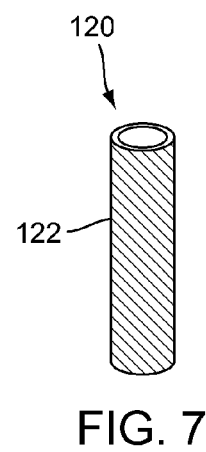
FIG. 6
FIG. 7
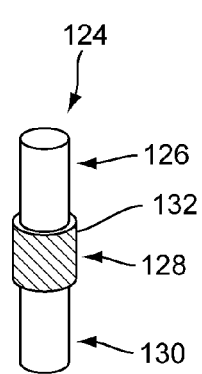
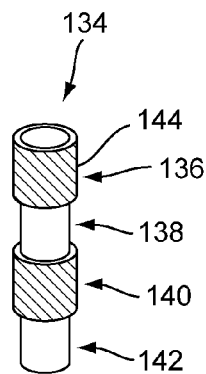
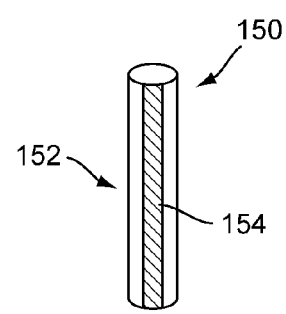
FIG. 8
FIG. 9
FIG. 10
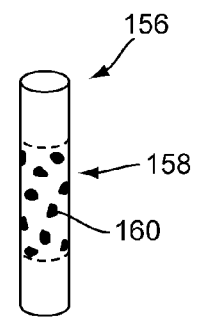
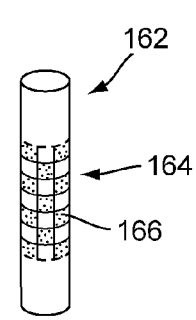
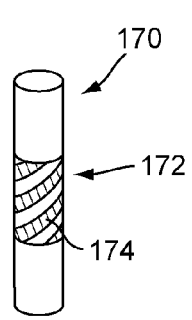
FIG. 11
FIG. 12
FIG. 13

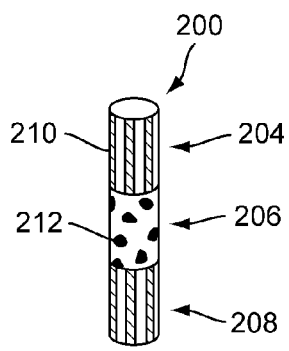 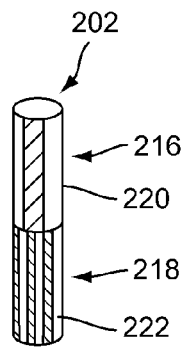 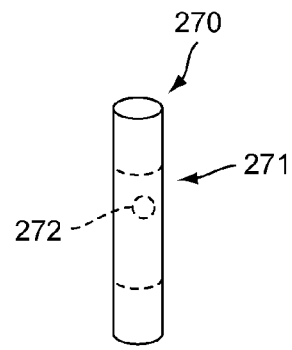
FIG. 14    FIG. 15    FIG. 16
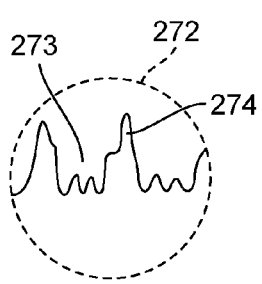 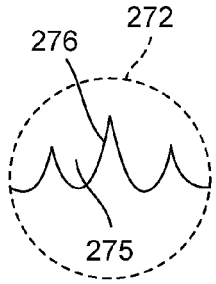 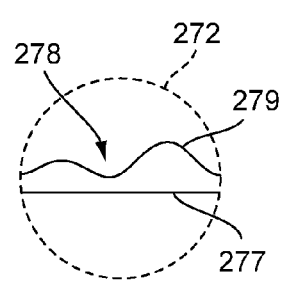
FIG. 17    FIG. 18    FIG. 19
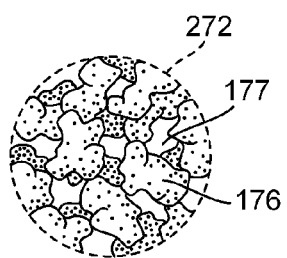 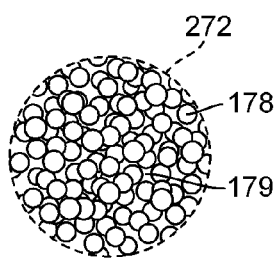 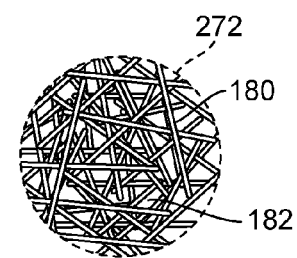
FIG. 20    FIG. 21    FIG. 22

PROSTHESIS WITH A SELECTIVELY APPLIED BONE GROWTH PROMOTING AGENT

CROSS REFERENCE TO RELATED APPLICATION

This application is a division of U.S. Patent Publication Number US 2008/0269893, published Oct. 30, 2008 (U.S. patent application Ser. No. 11/740,181, filed Apr. 25, 2007), which is herein incorporated herein by reference in its entirety.

BACKGROUND OF THE INVENTION

1. Field of the Invention

The present invention relates generally to implantable prostheses and in particular to prostheses including a selectively applied bone growth promoting agent.

2. Description of Related Art

Currently, only implantable hip and knee prostheses include some type of provision that promotes bone growth. In the past, various types of treatments or modifications to the surface of these prosthesis have been included that promote bone growth.

Screws with porous surfaces have been proposed. Serbousek (U.S. Pat. No. 5,098,434) teaches a screw for mounting a prosthetic component onto an underlying bone. The screw includes a head and an elongated cylindrical shank that is integral with and extends from the head. The shank includes a threaded member and a shoulder member having an outer surface with a porous medium for encouraging bone ingrowth fixation. The Serbousek screw is utilized in securing a hip prosthesis (acetabular cup) to the pelvis.

These screws are involved in securing the implants into one boney surface, for example, femeral stem component to the femur, an acetabular cup to the pelvis, distal femeral knee prosthesis to the femur or a tibial component to the tibia.

Tharmann (U.S. Pat. No. 5,360,448) teaches another porous-coated bone screw for securing a joint prosthesis. In the design of Tharmann, bone screws are proposed with and without heads. The bone screws include a shaft provided with axially adjacent longitudinally extending portions. These extending portions include bone ingrowth porous surfaces and alternate with portions having threaded surfaces.

While the related art teaches various forms of hip and knee prostheses with provisions for promoting bone growth, there are no provisions made for these surfaces and coatings being applied to trauma implants, fracture devices and implants, and fusion implants including rods, screws, plates and fusion cages. Related art prostheses lack selectively applied bone growth promoting treatments, and bone growth promoting treatments are not applied to general orthopedic implants. Generally, the bone growth treatments are applied along the prosthesis used in joint replacements and have been described only inside cylindrical threaded fusion cages. In these fusion cages, the bone promoting agent (BMP, OP1) is placed within the cage and its purpose is to allow for bony growth through the cage from one vertebra to another, in order to create a fusion. These bone growth treatments are not applied to the surface of the implants, and therefore do not induce the incorporation of the bone to the implant itself. The prior art does not teach the selective application of the variety of known bone growth promoting treatments for use in general orthopedic implants.

Additionally, the prostheses disclosed in the prior art do not include through-holes that permit bony integration into the implant. This refers to the fact that hip and knee prostheses are flat surfaces without holes. Also, pattern specificity is not disclosed in the prior art. Currently, hip and knee prosthesis only includes a partial coating to the proximal portion to the hip prosthesis but this technique is not used in general orthopedic implants.

Additionally, the prostheses disclosed in the prior art do not include through-holes that permit bone integration. Also, pattern specificity is not disclosed in the prior art. There is therefore a need in the art for prostheses that incorporate selectively applied bone growth promoting treatments.

SUMMARY OF THE INVENTION

An implantable prosthesis system, including a selectively applied bone growth promoting agent is disclosed. In one aspect, the invention provides an implantable prosthesis system, comprising: a rod configured for implantation into a bone; the rod including a first portion and a second portion; a bone growth promoting agent; and where the bone growth promoting agent is selectively applied to the first portion.

In another aspect, the rod has a solid core.

In another aspect, the rod includes a third portion and a fourth portion.

In another aspect, the bone growth promoting agent is selectively applied to the first and the third portion.

In another aspect, the rod includes holes.

In another aspect, the bone growth promoting agent is applied to the entire rod.

In another aspect, the bone growth promoting agent is disposed in a pattern selected from the group consisting essentially of striped patterns, spotted patterns, diagonal patterns, geometric patterns, shapes, and any combination thereof.

In another aspect, the invention provides an implantable prosthesis system, comprising: a rod configured for implantation into a bone; a sheet material including a bone growth promoting agent; and where the sheet material is associated with the rod.

In another aspect, the sheet material is selected from the group consisting essentially of continuous fabrics, mesh fabrics, collagens, biologic matrices, metallic foils, and plastic sheets.

In another aspect, the sheet material may be cut to a preconfigured size.

In another aspect, the sheet material may be cut to a preconfigured shape.

In another aspect, the sheet material is attached to the rod with an attachment selected from the group consisting essentially of an adhesive, hooks, microscopic hooks, temperature difference, interference fit, a Morris taper, and magnetic features.

In another aspect, the sheet material is rolled around the rod.

In another aspect, the invention provides an implantable prosthesis system, comprising: a rod configured for implantation into a bone; the rod having a hollow central core; the rod also having at least one hole placing the hollow central core in fluid communication with an exterior surface of the rod; and a bone growth promoting agent selectively applied to the exterior surface of the rod.

In another aspect, the rod includes holes along the entirety of its length.

In another aspect, the bone growth promoting agent is also applied to an inner surface of the hollow central core.

In another aspect, the bone growth promoting agent is disposed in at least one wall of the hole.

In another aspect, the rod includes a plurality of holes.

In another aspect, the holes are disposed along the entirety of the rod.

In another aspect, the invention provides a method of fusing an implantable prosthesis to a bone, comprising the steps of: selecting a rod with a selectively applied bone growth promoting agent, including an outer surface, an inner surface and a set of holes disposed between the outer surface and the inner surface; implanting the rod inside the bone; and allowing bone to grow into at least one hole of the set of holes.

In another aspect, the bone is allowed to grow into a hollow central core.

In another aspect, a portion of the bone fuses inside the hollow central core.

In another aspect, the bone growth promoting agent is selectively applied to the outer surface.

In another aspect, the bone growth promoting agent is selectively applied to the inner surface.

In another aspect, the bone growth promoting agent is selectively applied to the hole.

In another aspect, the invention provides an implantable prosthesis system, comprising: a fracture plate configured to be attached to a bone; the fracture plate including a first portion and a second portion along a lower surface; and wherein a bone growth promoting agent is selectively applied to the first portion of the lower surface.

In another aspect, the fracture plate includes holes.

In another aspect, the fracture plate includes a third portion.

In another aspect, the bone growth promoting agent is selectively applied to the first and the third region.

In another aspect, the bone growth promoting agent is disposed in a pattern selected from the group consisting essentially of striped patterns, spotted patterns, diagonal patterns, geometric patterns, shapes, and any combination thereof.

In another aspect, the fracture plate includes at least one hole configured to receive a screw.

In another aspect, the fracture plate includes two holes, each hole being configured to receive a screw.

In another aspect, the fracture plate includes more than two holes.

In another aspect, the invention provides an implantable prosthesis system, comprising: a fracture plate configured to be attached to a bone; the fracture plate including a recess configured to receive a liner; the liner including a first portion and a second portion along a lower surface configured to contact the bone; and where a bone growth promoting agent is selectively applied to the first portion of the lower surface.

In another aspect, the depth of the recess is approximately equal to the thickness of the liner.

In another aspect, the liner is a wafer of bone.

In another aspect, the liner is attached to the fracture plate with an attachment selected from the group consisting essentially of an adhesive, hooks, microscopic hooks, temperature difference, interference fit, a Morris taper, and magnetic features.

In another aspect, the bone growth promoting agent is disposed in a pattern selected from the group consisting essentially of striped patterns, spotted patterns, diagonal patterns, geometric patterns, shapes and any combination thereof.

In another aspect, the invention provides an implantable prosthesis system, comprising: a fracture plate including at least one hole disposed along a lower surface; the lower surface including a first region and a second region; and where a bone growth promoting agent is selectively applied to the first region and at least one hole.

In another aspect, the fracture plate includes many holes.

In another aspect, the holes are disposed along the entirety of the lower surface.

In another aspect, the holes include a bone growth promoting agent.

In another aspect, the holes contact a tissue adjacent to the bone.

In another aspect, the invention provides an implantable prosthesis system, comprising: a screw configured for insertion into a bone; the screw including threading; the threading including threading peaks and threading valleys; a bone growth promoting agent; and where the bone growth promoting agent is selectively applied to a portion of the threading.

In another aspect, the bone growth promoting agent is selectively applied to at least one of the group consisting essentially of the threading valleys, the threading peaks, upper portions of the threading, lower portions of the threading, middle portions of the threading and any combination thereof.

In another aspect, the bone growth promoting agent is applied to the entire threading.

In another aspect, the screw includes at least one hole.

In another aspect, a bone growth promoting agent is selectively applied to at least one wall of the hole.

In another aspect, the screw includes multiple holes.

In another aspect, the screw includes a hollow central core.

In another aspect, the screw includes a boring tip.

In another aspect, the screw includes a screw head.

In another aspect, the invention provides an implantable prosthesis system, comprising: a screw configured for insertion into a bone; the screw including a cavity; the cavity including an inner surface; and where a bone growth promoting agent is selectively applied along the inner surface.

In another aspect, the screw includes a boring tip.

In another aspect, the screw includes a screw head.

In another aspect, the screw includes at least one hole.

In another aspect, a bone growth promoting agent is selectively applied to at least one wall of the hole.

In another aspect, the screw includes multiple holes.

In another aspect, the outer surface and the inner surface are in fluid communication through at least one hole.

All of the various implants discussed above including screws, fracture plates, cages, connectors, wires, cables, clamps, staples, anchors or any other kind of prosthesis can be composed of any suitable orthopedic material, including titanium, cobalt—chrome, stainless steel, carbon fiber, polymer matrix, bony material, allograft, or any other orthopedically acceptable material. Regardless of the material, in some embodiments, selected portions of the surface can include bone growth provisions that encourage bone growth into the material itself. This surface treatment can include hydroxy apetite, plasma spray, sintering, micro porous beads, ceramic, calcium phosphate coatings or matrices; collagen matrix, or other porous coatings or fiberous arrays.

Other systems, methods, features, and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 6 is an isometric view of a preferred embodiment of a rod and a sleeve;

FIG. 7 is an isometric view of a preferred embodiment of a rod with a bone growth promoting agent;

FIG. 8 is an isometric view of a preferred embodiment of a rod with a bone growth promoting agent applied along a single portion;

FIG. 9 is an isometric view of a preferred embodiment of a rod with a bone growth promoting agent applied along several portions;

FIG. 10 is an isometric view of a preferred embodiment of a rod with a bone growth promoting agent applied as a striped pattern;

FIG. 11 is an isometric view of a preferred embodiment of a rod with a bone growth promoting agent applied as a spotted pattern;

FIG. 12 is an isometric view of a preferred embodiment of a rod with a bone growth promoting agent applied as a geometric pattern;

FIG. 13 is an isometric view of a preferred embodiment of a rod with a bone growth promoting agent applied as a spiral pattern;

FIG. 14 is an isometric view of a preferred embodiment of a rod with a bone growth promoting agent applied as various patterns;

FIG. 15 is an isometric view of a preferred embodiment of a rod with a bone growth promoting agent applied as various patterns;

FIG. 16 is an isometric view of a preferred embodiment of a rod with a modified surface texture;

FIG. 17 is a side view of a preferred embodiment of a microscopic surface texture;

FIG. 18 is a side view of a preferred embodiment of a microscopic surface texture;

FIG. 19 is a side view of a preferred embodiment of a microscopic surface texture;

FIG. 20 is a top down view of a preferred embodiment of a three dimensional surface texture;

FIG. 21 is a top down view of a preferred embodiment of a three dimensional surface texture;

FIG. 22 is a top down view of a preferred embodiment of a three dimensional surface texture;

DETAILED DESCRIPTION OF THE PREFERRED EMBODIMENTS

Figure 1:
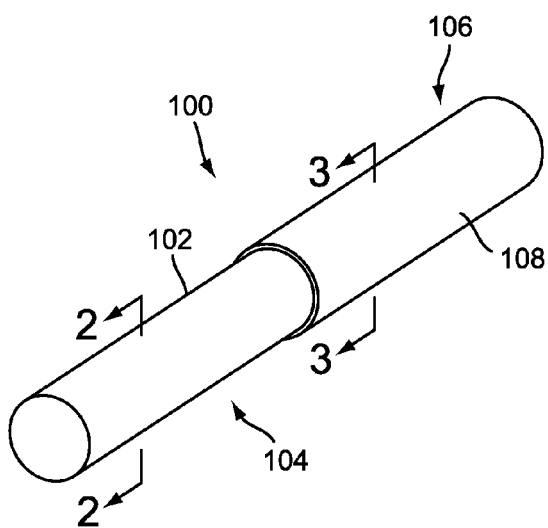
FIG. 1 is an isometric view of a preferred embodiment of a rod.

FIG. 1 is a preferred embodiment of an implantable prosthesis in the form of rod 100. For clarity, the following detailed description discusses a preferred embodiment; however, it should be kept in mind that the present invention could also take the form of any other kind of implantable prosthesis including, for example, screws, fracture plates, cages, connectors, wires, cables, clamps, staples, anchors or any other kind of prosthesis.

Often, an implantable prosthesis may include a provision for promoting bone growth. Generally, throughout this specification and the claims, such a provision will be referred to as a bone growth promoting agent. Bone growth promoting agents may be divided into two categories. The first category includes any provision that uses additive components to the prosthesis itself. The second category includes any provision that modifies the surface structure of the prosthesis, which is often metallic.

The first category may include provisions that are freeze dried onto a surface or adhered to the metal through the use of linker molecules or a binder. Examples of the first category that may be applied through these techniques include, but are not limited to, bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix, or gel.

Some chemicals from the first category may also be applied to an implantable prosthesis through the use of a plasma spray or electrochemical techniques. Examples of these chemicals include, but are not limited to, hydroxyapatite, beta tri-calcium phosphate, calcium sulfate, calcium carbonate, as well as other chemicals.

Provisions from the second category generally modify the surface structure of the prosthesis. In some cases, the surface structure is roughened or provided with irregularities. Generally, this roughened structure may be accomplished through the use of acid etching, bead or grit blasting, sputter coating with titanium, sintering beads of titanium or cobalt chrome onto the implant surface, as well as other methods. This can result in a prosthesis with a surface roughness with about 3-5 microns of roughness peak to valley. However, in some embodiments, the surface roughness may be less than 3-5 microns peak to valley, and in other embodiments, the surface roughness may be greater than 3-5 microns peak to valley. In some exemplary embodiments, the prosthesis can be made of commercially pure titanium or a titanium alloy (such as Ti6Al4V) with about 3-5 microns of roughness peak to valley.

It should be understood that the provisions listed here are not meant to be an exhaustive list of possible bone growth promoting agents. The term bone growth promoting agent, as used in this specification and claims, is intended to include any method of modifying an implantable prosthesis that stimulates bone growth either directly or indirectly.

Rod 100 preferably includes outer surface 102. In some embodiments, outer surface 102 preferably includes first portion 104 and second portion 106. In this embodiment, coating 108 has been applied to second portion 106 of outer surface 102. In a preferred embodiment, coating 108 includes a bone growth promoting agent of some kind.

Figure 2:
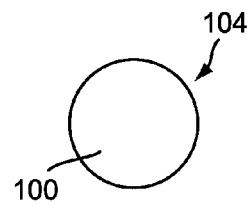
FIG. 2 is a cross sectional view of a preferred embodiment of a rod.
Figure 3:
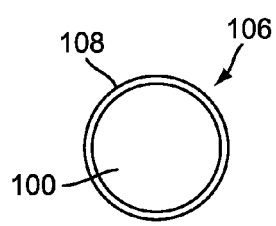
FIG. 3 is a cross sectional view of a preferred embodiment of a rod.

Referring to FIGS. 2-3, cross sections of first portion 104 and second portion 106 preferably differ. In particular, second portion 106 preferably includes coating 108. In this embodiment, coating 108 preferably has some thickness. In other embodiments, the thickness of coating 108 may be varied.

As previously mentioned, bone growth promoting agents may be applied in a variety of ways. In some embodiments, bone growth promoting agents may be applied to a mesh or fabric material that may be independently manufactured from the implantable prosthesis. In this manner, the fabric or mesh material, which includes the bone growth promoting agent, may be applied to the implantable prosthesis at any time prior to surgery, during surgery or even after implantation. In addition to mesh or a fabric material, the sheet can be any kind of bio-compatible material that includes a metallic foil, a plastic sheet, or a biological matrix. The metal can be titanium, stainless steel, cobalt chrome or any other type of bio-compatible metal or matrix.

Figure 4:
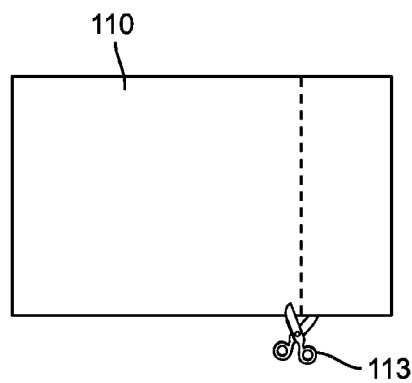
FIG. 4 is a plan view of a preferred embodiment of a sheet material.
Figure 5:
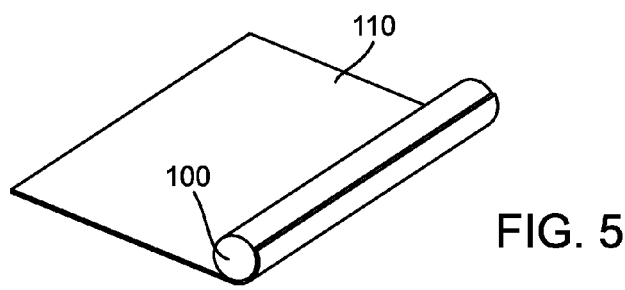
FIG. 5 is an isometric view of a preferred embodiment of a sheet material being applied to a rod.

Referring to FIGS. 4-5, sheet material 110 may be constructed to include a bone growth promoting agent. In some embodiments, sheet material 110 may be any material that may be configured to include a bone growth promoting agent, and that is flexible enough to wrap around an implantable prosthesis. In a preferred embodiment, sheet material 110 may be a mesh or continuous fabric. In this embodiment, scissors 113 may be used to cut sheet material 110 to a preconfigured size, which can be any desired size.

Once sheet material 110 has been cut to an appropriate size, it may be applied to rod 100. Generally, sheet material 110 may be rolled over rod 100. In some embodiments, sheet material 110 may be attached to rod 100 through an adhesive. It is also possible to attach sheet material 110 to rod 100 by using mechanical provisions, including hooks, microscopic hooks, temperature difference, interference fit, or a Morris taper. It is also possible to attach sheet material 110 to rod 100 using magnetic features. In a preferred embodiment, sheet material 110 may be preconfigured to include an adhesive for attaching to rod 100.

In some embodiments, a sheet material may be preconfigured as a sleeve or any desired shape. Preferably, the sleeve may be configured so that a rod or another type of prosthesis may be inserted into the sleeve, without the need to wrap the sheet material around the prosthesis. The sleeve can come in a variety of sizes and shapes. Like the sheet material, the sleeve material may be constructed of a continuous or mesh fabric, collagen, or biologic matrix, metallic foil or plastic sheet.

Referring to FIG. 6, sleeve material 112 may be constructed to include a bone growth promoting agent. Preferably, sleeve material 112 may be configured to receive all or a portion of a rod 100. Generally, sleeve material 112 may be configured to receive all or a portion of an implantable prosthesis. In this manner, a bone growth promoting agent may be applied via sleeve material 112 by simply inserting the prosthesis into sleeve material 112. This configuration allows a bone growth promoting agent to be applied to a rod in an efficient manner.

Preferably, sheet material 110 and sleeve material 112 may be applied to multiple types of implantable prosthesis, including, but not limited to screws, fracture plates, cages, connectors, wires, cables, clamps, staples, anchors, or any other kind of prosthesis. In some embodiments, sheet material 110 may be cut to a size configured to cover all or a portion of an implantable prosthesis. Additionally, sleeve material 112 may be constructed in a manner that allows all or a portion of an implantable prosthesis to be inserted into sleeve material 112.

Preferably, a rod intended to be used as a prosthesis includes provisions for selectively applying a bone growth promoting agent to various portions of the rod. In other words, a bone growth promoting agent need not be applied to the entirety of the rod. Instead, the bone growth promoting agent may be applied to a single portion of the rod. In some embodiments, the bone growth promoting agent may be applied to multiple, but not all, portions of the rod. Additionally, the bone growth promoting agent may be applied differently along different portions of the rod. In this manner, the rod may be used to differentially stimulate bone growth along various portions of the adjacent bone to simulate fusion, healing, stabilization, and/or incorporation. This may be useful in cases where some, but not all, portions of the bone are damaged.

Referring to FIGS. 7-9, several embodiments of a rod may include a bone growth promoting agent that has been applied along various portions. For the purposes of illustration, the thicknesses of the portions including a bone growth promoting agent have been exaggerated. Generally, these thicknesses may vary. Some bone growth promoting agents may be applied to the surface of a rod, or other prosthesis, and have no visible thickness.

In some embodiments, the bone growth promoting agent may be applied to the entirety of the rod. Rod 120 preferably includes bone growth promoting agent 122 along the entirety of the length of rod 120. Bone growth promoting agent 122 may be any of the possible provisions discussed previously for applying a bone growth promoting agent to an implantable prosthesis. With this configuration, rod 120 may help to stimulate bone growth along the entirety its length, following the implantation of rod 120.

In other embodiments, a rod may include three portions, with only one portion including a bone growth promoting agent. Rod 124 preferably includes first portion 126, second portion 128, and third portion 130. In a preferred embodiment, second portion 128 includes bone growth promoting agent 132. With this configuration, rod 124 may help to stimulate bone growth along a portion of the bone adjacent to second portion 128, following the implantation of rod 124.

In another embodiment, a rod may include four portions, with alternating portions including a bone growth promoting agent. Preferably, rod 134 may include first portion 136, second portion 138, third portion 140, and fourth portion 142. In some embodiments, only first portion 136 and third portion 140 include bone growth promoting agent 144. With this configuration, rod 134 may help to stimulate bone growth along portions of the bone adjacent to first portion 136 and third portion 140, following the implantation of rod 134. In other embodiments, more or less than four portions may be provided.

In the previous embodiments, along portions where a bone growth promoting agent has been applied, it has been preferably applied uniformly throughout the portion. In some embodiments, however, a bone growth promoting agent may be applied in particular patterns throughout a portion. Depending on the circumstances, different types of patterns may be used to promote bone growth.

Examples of some patterns include stripes, spots, helical or spiral, geometric patterns, or combinations incorporating one or more of these basic pattern elements. The term geometric pattern refers to any polygonal pattern including square (shown in the Figures), rectangular, polygon, honeycomb, repeating, non-repeating, regular, irregular, as well as other types of patterns. A striped pattern includes thin lines of bone growth promoting agent that are disposed along a particular portion. In this arrangement, there is no bone growth promoting agent between the stripes. A spotted pattern may include small spots of the bone growth promoting agent. In a similar manner, a geometric pattern may include alternating shapes of a bone growth promoting agent. Various patterns may be used depending on the way in which the user wants to induce bone growth along or adjacent to the prosthetic.

FIGS. 10-13 illustrate various patterns of bone growth promoting agents applied to rods. Rod 150 preferably includes first portion 152. In some embodiments, first portion 152 may include bone growth promoting agent 154. In a preferred embodiment, bone growth promoting agent 154 may be disposed in a striped pattern as shown in FIG. 10. This striped pattern may include one or more stripes. Generally, the thickness and/or density of these stripes may be varied. Additionally, their orientation may also be varied. The shape, density, and/or distribution of the bone growth promoting agent will allow for selectively tailored bone growth or fusion.

In a second embodiment, rod 156 preferably includes first portion 158. In some embodiments, first portion 158 may include bone growth promoting agent 160. In a preferred embodiment, bone growth promoting agent 160 may be disposed in spots along first portion 158. Generally, the shape and/or density of these spots may be varied.

In a third embodiment, rod 162 preferably includes first portion 164. In some embodiments, first portion 164 may include bone growth promoting agent 166. In a preferred embodiment, bone growth promoting agent 166 may be disposed in a geometric pattern along first portion 164. Generally, the size of the squares comprising this geometric pattern may be varied.

In a fourth embodiment, rod 170 preferably includes first portion 172. In some embodiments, first portion 172 may include bone growth promoting agent 174. In a preferred embodiment, bone growth promoting agent 174 may be disposed in a spiral or helical pattern along first portion 172. Generally, the thickness and spacing of this spiral pattern may be varied.

The patterns disclosed here are not intended to be exhaustive, but only illustrative of the various types of patterns that may be included in portions where a bone growth promoting agent is applied to a rod or other implantable prosthesis. Generally, any type of pattern may be used. Additionally, within the same portion, multiple patterns may be superimposed.

Generally, various patterns of bone growth promoting agents may be selectively applied to multiple portions of a rod or other implantable prostheses. FIGS. 14-15 are a preferred embodiment of first rod 200 and second rod 202. In some embodiments, first rod 200 includes first portion 204, second portion 206, and third portion 208. In some embodiments, a distinct pattern of a bone growth promoting agent may be selectively applied to each of the portions 204, 206, and 208. In a preferred embodiment, first portion 204 and third portion 208 may include bone growth promoting agent 210 arranged as stripes. Likewise, second portion 206 may include bone growth promoting agent 212 arranged as spots.

Preferably, second rod 202 includes first portion 216 and second portion 218. In some embodiments, both first portion 216 and second portion 218 include the same pattern of a bone growth promoting agent. In some embodiments, both portions 216 and 218 include a bone growth promoting agent arranged as stripes. In some embodiments, first portion 216 includes first striped pattern 220 of a bone growth promoting agent, while second portion 218 includes second striped pattern 222 of a bone growth promoting agent. In a preferred embodiment, the density of first striped pattern 220 is lower than the density of second striped pattern 222. First striped pattern 220 can have a different orientation and can be angled with respect to second striped pattern 222.

Referring to FIGS. 16-22, bone growth promoting agents may also be selectively applied to various portions of a rod by modification of the surface properties. Preferably, rod 270 includes first portion 271. In some embodiments, first portion 271 may include a bone growth promoting agent in the form of a textured surface. The structure of this surface may be seen in a close up of patch 272.

In some embodiments, first portion 271 may include a textured surface due to acid etching of titanium. In this case, a side view of patch 272, when viewed at the microscopic level, may include jagged peaks 274 and jagged valleys 273. In another embodiment, first portion 271 may include a textured surface due to grit blasting the titanium. In this case, a side view of patch 272, when viewed at a microscopic level, may include sharp peaks 276 and smooth valleys 275. Finally, in an embodiment where plasma spraying is used to texture the surface of portion 271, a side view of patch 272 may include rounded peaks 279, rounded valleys 278, and under surface 277.

Referring to FIGS. 20-22, some rods may be configured so that the surface includes various three dimensional structures. In some embodiments, first surface 272 may include an irregular three dimensional surface. FIG. 20 shows an embodiment including an irregular porous titanium construct, including irregular structures 176 and first pores 177. In a preferred embodiment, the sizes of first pores 177 may be between 100 and 600 microns. In another embodiment, first surface 272 may include a regular three dimensional surface. FIG. 21 shows an embodiment including a regular ball bearing type structure made of titanium, including ball bearing-like structures 178 and second pores 179. Second pores 179 may also have a size between 100 and 600 microns. In another embodiment, shown in FIG. 22, first surface 272 may include a fibrous three dimensional surface. In this embodiment, the fibrous surface includes fibrous structures 180 and third pores 182. Using these various types of three dimensional structures on the surface of rod 270 allows for an increased surface area for new bone growth, as opposed to traditional surface treatment methods. In particular, the height or thickness of these various surface treatments may be large when compared with traditional surface treatments.

Other surface treatments that can be used include microporous coatings. Additionally, any and all coatings, treatments, or patterns can be used that promote bone growth or allow for bone growth to the prosthesis and effectively lock the prosthesis to the bone. In some embodiments, these surface treatments can provide the surface of the prosthesis with a roughness of about 3-5 microns, peak to valley, or a pore size of about 1-850 microns as previously discussed. The pore size can be increased if desired. However, in other embodiments, the peak to valley roughness will be greater than 3-5 microns, and in other embodiments, the peak to valley roughness may be less than 3-5 microns, depending on the application. In some cases, these surface treatments will be invisible to the naked eye.

The specific surface treatment feature or combination of features can be selected based on: biology, location, bony region (metaphyseal or cortical bone; weight bearing or non-weight bearing, for example) cost, strength of the implant or prosthesis, geometry or size of the implant or prosthesis and manufacturing feasibility, among other criteria or factors that may be considered.

Figure 23:
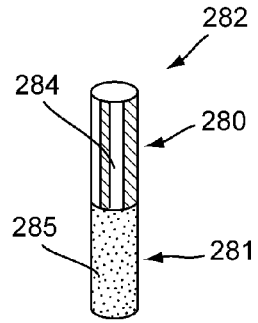
FIG. 23 is an isometric view of a preferred embodiment of a rod with various bone growth promoting agents.
Figure 24:
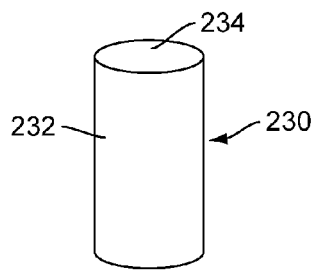
FIG. 24 is an isometric view of a preferred embodiment of a solid rod.
Figure 25:
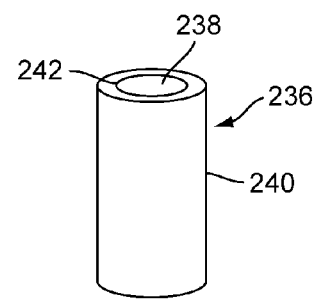
FIG. 25 is an isometric view of a preferred embodiment of a hollow rod.
Figure 26:
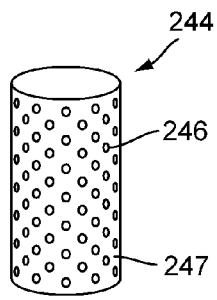
FIG. 26 is an isometric view of a preferred embodiment of a solid rod with holes.
Figure 27:
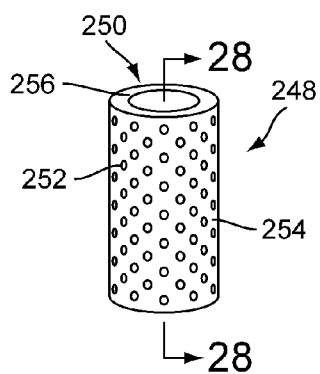
FIG. 27 is an isometric view of a preferred embodiment of a hollow rod with holes.

In some embodiments, a rod may include a chemical bone growth promoting agent along one portion and a modified surface bone growth promoting agent along a second portion. In a preferred embodiment, shown in FIG. 23, rod 282 may include first region 280 and second region 281. In some embodiments, each of the regions 280 and 281 may include a different bone growth promoting agent. In a preferred embodiment, first region 280 may include striped pattern 284 of a chemical bone growth promoting agent. Also, second region 281 may include acid etched surface 285, another type of bone growth promoting agent. For the purposes of illustration, acid etched surface 285 is shown here with some shading, but generally, textured surfaces may be invisible to the naked eye.

Generally, some rods include provisions for modifying the structure of the rod. These modifications may include a hollowing out of the core of the rod. Additionally, these modifications may include the addition of holes that may be disposed along the outer surface of the rod and penetrate into the core of the rod.

Referring to FIGS. 24-27, rods may be configured solid, hollow, and with or without holes. If the rod includes holes, the holes can be any desired size and shape. Also, the distribution pattern of the holes may be varied. In one embodiment, a section of rod 230 may be solid. Rod 230 may include outer surface 232. In a preferred embodiment, core 234 of rod 230 may be solid. In a second embodiment, a section of rod 236 may include hollow central core 238. Preferably, rod 236 includes outer surface 240. In a preferred embodiment, rod 236 may also include inner surface 242 of hollow central core 238.

Preferably, a third embodiment of a section of rod 244 may include holes 246. Holes 246 are preferably disposed along the entirety of rod 244 along outer surface 247. Holes 246 may also be disposed along a single portion of rod 244 in other embodiments. Generally, holes 246 may be any depth, any shape, angle, and have any size circumference. Similarly, the density of holes 246 may be varied in other embodiments. In some embodiments, a combination of holes having different sizes, shapes, angles, or densities may be used.

A fourth embodiment of a section of rod 248 may preferably include hollow central core 250 as well as holes 252. Holes 252 are preferably disposed along the entirety of rod 248. Generally, holes 252 may be any depth, any shape, angle, and have any size circumference. Similarly, the density of holes 252 may be varied in other embodiments. In some embodiments, a combination of holes having different sizes, shapes, angles, or densities may be used. Holes 252 may or may not penetrate through to hollow central core 250. In a preferred embodiment, holes 252 are disposed between outer surface 254 and inner surface 256 of hollow central core 250. In this manner, holes 252 preferably allow fluid communication between hollow central core 250 and outer surface 254, which allows bony ingrowth to occur into the interstices of rod 248.

Preferably, an implantable prosthesis system may include provisions for fusing the prosthesis to the bone. In some embodiments, a rod may be configured to be fused to a bone once it has been implanted. In particular, the rod may include provisions that allow the bone to penetrate through the outer surface and grow along an inner surface of a hollow core or into the holes themselves, and into the bone growth promoting agent of the prosthesis.

Figure 28:
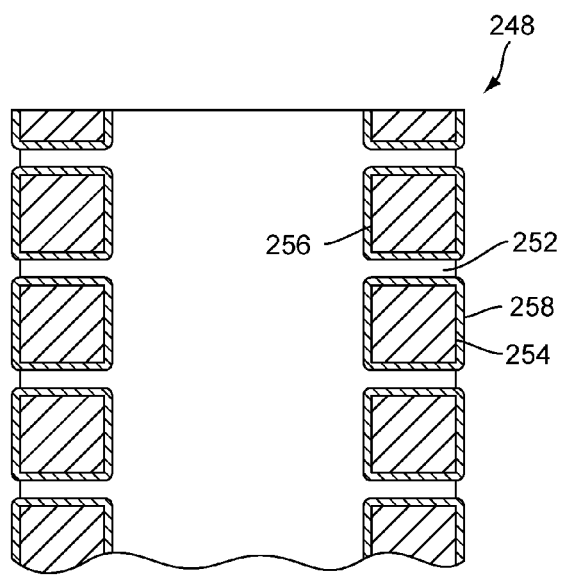
FIG. 28 is a schematic cross sectional view of a preferred embodiment of a hollow rod with holes.

In some embodiments, outer surface 254 may include bone growth promoting agent 258, seen in FIG. 28, a cross sectional view of rod 248. In some embodiments, inner surface 256 may also include bone growth promoting agent 258. Additionally, holes 252 may also be lined with bone growth promoting agent 258. This configuration preferably allows bone to grow along outer surface 254 as well as inner surface 256, via holes 252. Bone growth can also occur into the holes themselves, and into the bone growth promoting agent of the prosthesis.

Figure 29:
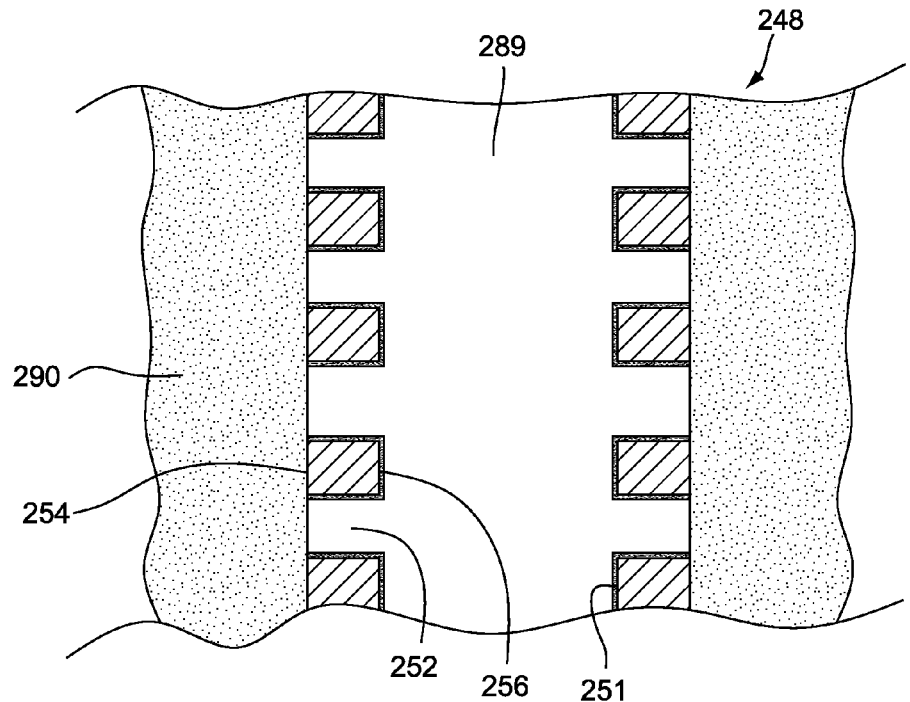
FIG. 29 is a schematic cross sectional view of a preferred embodiment of a rod inserted into bone.
Figure 30:
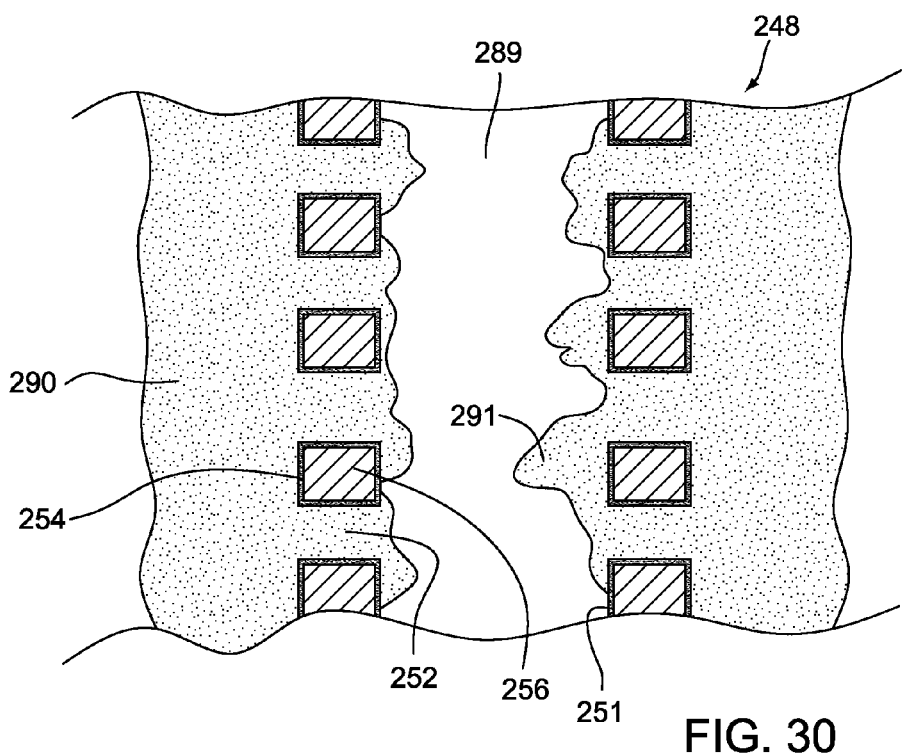
FIG. 30 is a schematic cross sectional view of a preferred embodiment bone growing into a rod.

Referring to FIGS. 29-30, ingrowth of the bone from outer surface 254 to inner surface 256 may proceed once rod 248 has been inserted into a section of bone 290 or surrounded by bone 290, whether from a fracture or fusion. With time, portions 291 of bone 290 may grow through holes 252 into hollow central core 289. In some embodiments, portions 291 may fuse together inside hollow central core 289. In this way, rod 248 may be fused with bone 290. In a preferred embodiment, holes 252 are used in conjunction with bone growth promoting agent 251 disposed along inner surface 256 and outer surface 254 in order to induce bone growth. In some embodiments, bone growth promoting agent 251 may also be disposed within holes 252. In this manner, rod 248 may be partially or fully integrated into bone 290 as it heals.

Generally, in the rod embodiment disclosed above, or in any of the embodiments disclosed below, a combination of macroscopic holes and microscopic holes or other bone growth promoting surface treatments can be used. By using a combination of both features, bone growth can be encouraged at the surface of the prosthesis so that the prosthesis, on a surface level, integrates with the bone; and by using macroscopic holes, large scale or bulk integration of the prosthesis can occur, further solidifying the integration of the prosthesis with the bone.

Figure 31:
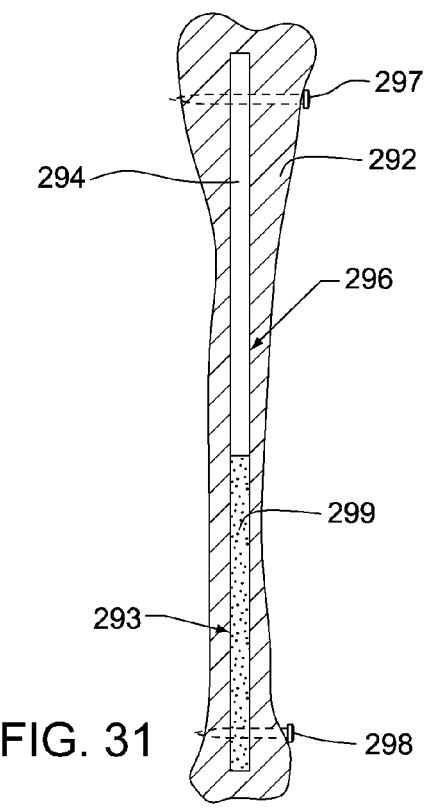
FIG. 31 is a cross sectional view of a preferred embodiment of an implantable prosthesis system.

FIG. 31 is a cross sectional view of a preferred embodiment of implantable prosthesis system 296. Preferably, implantable prosthesis system 296 is integrated into bone 292 (seen here in cross section). Preferably, implantable prosthesis system 296 may include rod 294, as well as first bone screw 297 and second bone screw 298. In some embodiments, rod 294 may include bone growth promoting agent 299, disposed along a first portion 293 of rod 294. First portion 293 can range from a relatively small portion of rod 294 to substantially all of rod 294. In some embodiments, second screw 298 may also be coated with bone growth promoting agent 299. Generally, any desired number of screws in system 296 can include bone growth promoting agents. It is also possible that the location of various, differently treated screws is varied depending on the type of bone. For example, a screw for use in cortical bone may have one type of bone growth promoting agent, while a screw for use in cancellous or spongy bone has a second type of bone growth promoting agent. In this manner, the portion of bone 292 disposed adjacent to first portion 293 of rod 294 and second screw 298 may be stimulated to grow and fuse around rod 294 and second screw 298.

In an alternative embodiment, the implantable prosthesis may take the form of a fracture plate. In a manner similar to the rods discussed in the previous embodiments, a bone growth promoting agent may be applied to a fracture plate to stimulate bone growth. In a preferred embodiment, a bone growth promoting agent may be selectively applied to various portions of a fracture plate, stimulating bone growth along various portions of the bone.

Figure 32:
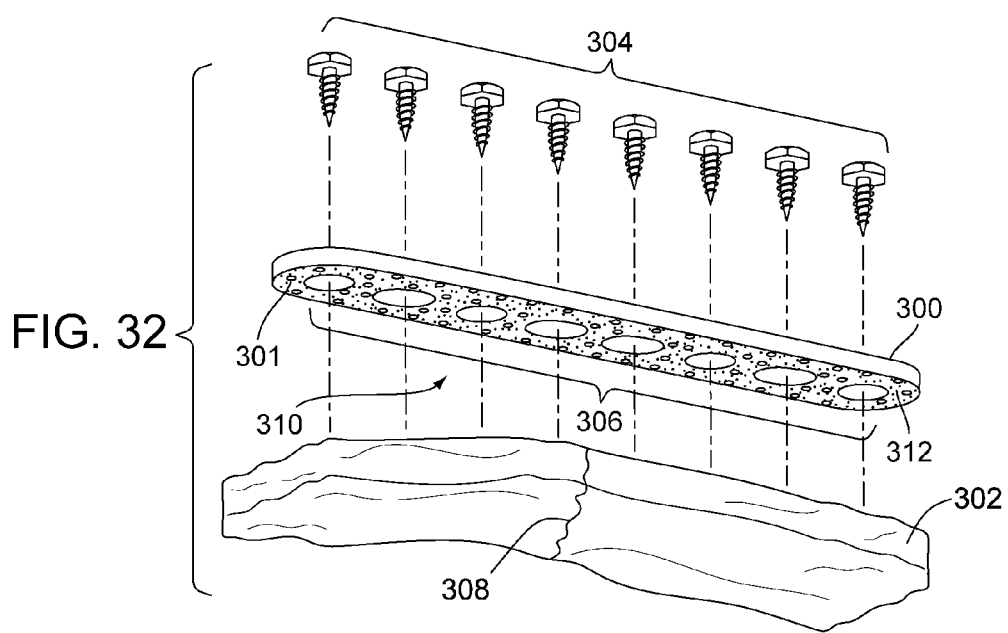
FIG. 32 is an isometric view of a preferred embodiment of a fracture plate configured to attach to a bone.
Figure 33:
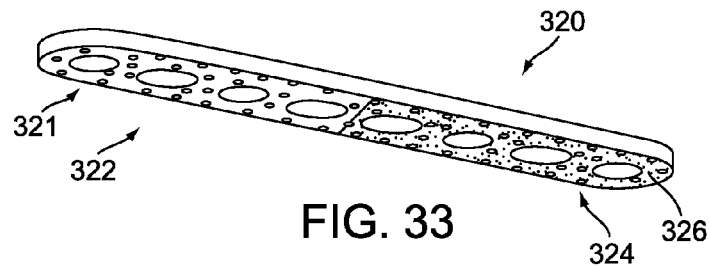
FIG. 33 is an isometric view of a preferred embodiment of a fracture plate with a bone growth promoting agent.
Figure 34:
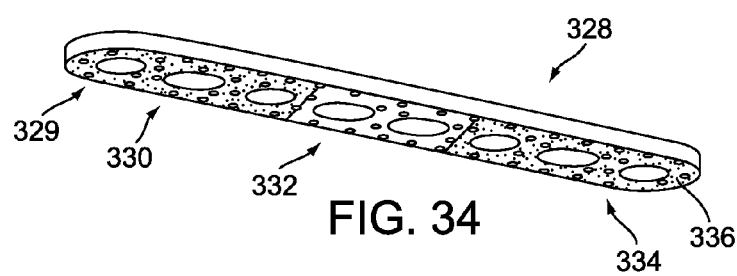
FIG. 34 is an isometric view of a preferred embodiment of a fracture plate with a bone growth promoting agent.
Figure 35:
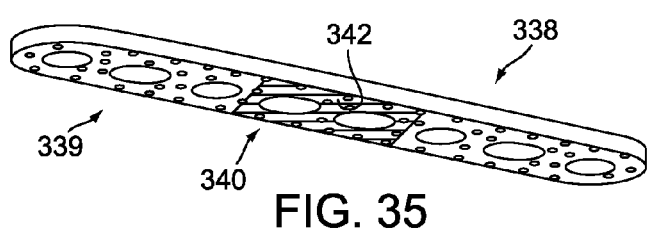
FIG. 35 is an isometric view of a preferred embodiment of a fracture plate with a bone growth promoting agent.
Figure 36:
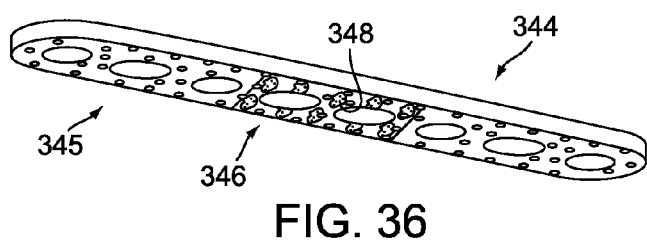
FIG. 36 is an isometric view of a preferred embodiment of a fracture plate with a bone growth promoting agent.
Figure 37:
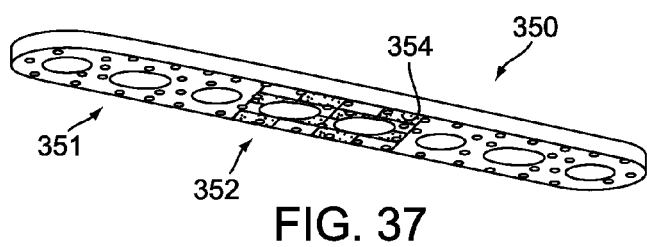
FIG. 37 is an isometric view of a preferred embodiment of a fracture plate with a bone growth promoting agent.
Figure 38:
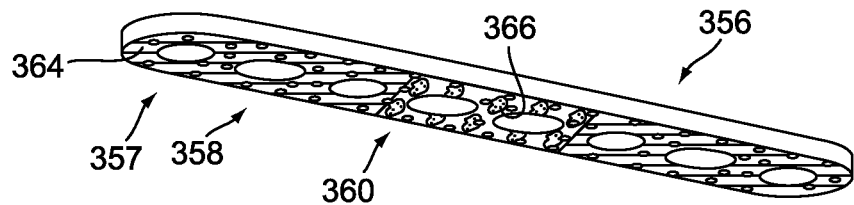
FIG. 38 is an isometric view of a preferred embodiment of a fracture plate with a bone growth promoting agent.
Figure 39:
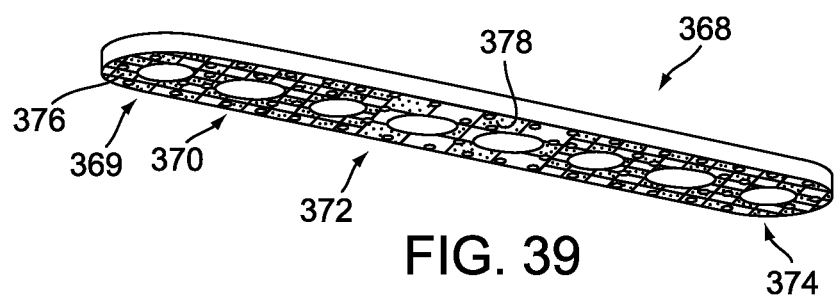
FIG. 39 is an isometric view of a preferred embodiment of a fracture plate with a bone growth promoting agent.

FIG. 32 is an exploded isometric view of a preferred embodiment of fracture plate 300 that may be attached to bone 302. Generally, fracture plate 300 may be attached to bone 302 using screw set 304. The screws comprising screw set 304 may be inserted through screw hole set 306 of fracture plate 300. With this arrangement, fracture plate 300 may be attached to bone 302 in order to add support to bone 302 while fracture 308 heals. Generally, any number of screws and screw holes may be used. In this exemplary embodiment, there are eight screws comprising screw set 304 and eight screw holes comprising screw hole set 306.

In the preferred embodiments, the profile of fracture plate 300 is minimized by the long and narrow shape of fracture plate 300. Additionally, the profile may be minimized by the use of large screw holes. This reduction in profile may decrease the tendency of fracture plate 300 to interfere with the surrounding tissue and may also help decrease the weight of fracture plate 300 while maintaining a high density for strength and durability.

In the preferred embodiment, fracture plate 300 may also include small holes 301 that are disposed on lower surface 310. Small holes 301 may be macro and/or micro holes. Small holes 301 may extend partially into fracture plate 300, or may extend all the way through. Also, small holes 301 may be disposed anywhere on lower surface 310, in any pattern, including a random pattern. The use of small holes 301 preferably facilitates both macro and micro fixation of bone growth.

In some embodiments, fracture plate 300 may include a lower surface 310. In some embodiments, lower surface 310 may be coated with bone growth promoting agent 312. Preferably, in this embodiment, bone growth promoting agent 312 may cover the entirety of lower surface 310. Generally, bone growth promoting agent 312 may be any of the types of bone growth promoting agents discussed previously.

In some embodiments, an intermediate tissue or membrane is disposed between fracture plate 300 and bone 302. In other words, fracture plate 300 may not directly contact bone 302. Instead, fracture plate 300 may be configured to contact some other tissue or membrane disposed adjacent to bone 302. This membrane can include muscle or periosteum.

As with the rods in the previous embodiments, bone growth promoting agents may be selectively applied to various portions of fracture plates. In this way, different portions of a bone in contact with a fracture plate may be stimulated to grow differently. Generally, a bone growth promoting agent may be applied to any portion of a fracture plate. Additionally, a bone growth promoting agent may be disposed in any pattern along the fracture plate. This may be useful in cases where some, but not all, portions of the bone are damaged.

Referring to FIGS. 32-41, bone growth promoting agents may be applied to a fracture plate in a variety of ways. The following embodiments are intended to illustrate possible configurations of fracture plates including one or more bone growth promoting agents; however it should be understood that these embodiments are only intended to be exemplary. Many other types of bone growth promoting agents, including various patterns may be applied to one or multiple portions of a fracture plate. Additionally, throughout the following embodiments, the bone growth promoting agents may be used in combination with macro and micro holes in order to further facilitate bony fusion.

First plate 320 preferably includes first lower surface 321. In some embodiments, first lower surface 321 may include first portion 322 and second portion 324. In some embodiments, first portion 322 and second portion 324 may have different treatments. In a preferred embodiment, first portion 322 is not treated. In a preferred embodiment, second portion 324 may be treated with bone growth promoting agent 326.

As previously discussed, bone growth promoting agent 326 may include chemical treatments of the surface, or modifications to the texture of the surface of the prosthesis. Generally, the bone growth promoting agent applied to a fracture plate may be any type of bone growth promoting agent discussed in the previous embodiments involving rods, as well as any other bone growth promoting agent. In these embodiments, the bone growth promoting agents are visually distinct from the general surface to which they are applied. However, this is done purely for illustrative purposes. In some embodiments, the bone growth promoting agents may not be visible.

Second fracture plate 328 also preferably includes several portions. In some embodiments, second plate 328 may include lower surface 329. In some embodiments, second lower surface 329 may include first portion 330, second portion 332, and third portion 334. In some embodiments, first portion 330 and third portion 334 may be treated in a similar manner. In a preferred embodiment, first portion 330 and third portion 334 both include bone growth promoting agent 336. In this manner, second fracture plate 328 preferably helps to induce growth along portions of the bone adjacent to first portion 330 and third portion 334, but not second portion 332.

Additionally, fracture plates may be treated with a bone growth promoting agent that is disposed along the outer surface in a variety of designs. These designs may be similar to the designs discussed in previous embodiments, or other types of designs. In some embodiments, fracture plates may include a bone growth promoting agent applied in striped, spotted, geometric patterns, and/or combinations of two or more of these basic patterns.

Third fracture plate 338 preferably includes center portion 340 disposed along lower surface 339. In some embodiments, center portion 340 may include a bone growth promoting agent. In a preferred embodiment, center portion 340 includes bone growth promoting agent 342 configured in a striped pattern.

In another embodiment, fourth fracture plate 344 also preferably includes center portion 346 disposed along lower surface 345. In some embodiments, center portion 346 may include a bone growth promoting agent. In a preferred embodiment, center portion 346 may include bone growth promoting agent 348 configured in a spotted pattern.

In another embodiment, fifth fracture plate 350 also preferably includes center portion 352 disposed along lower surface 351. In some embodiments, center portion 352 may include a bone growth promoting agent. In a preferred embodiment, center portion 352 preferably includes bone growth promoting agent 354 configured in a geometric pattern.

In another embodiment, sixth fracture plate 356 may include three separate portions. Preferably, sixth fracture plate 356 includes first portion 358, second portion 360, and third portion 362 disposed along lower surface 357. In some embodiments, each portion may be treated with a different bone growth promoting agent. In some embodiments, first portion 358 and third portion 362 may be treated with a similar pattern of bone growth promoting agent. In a preferred embodiment, first portion 358 and third portion 362 may include bone growth promoting agent 364 configured in a striped pattern. Also, second portion 360 may preferably include bone growth promoting agent 366 configured in a spotted pattern.

In some cases, different portions may be treated with the same pattern of bone growth promoting agents, but the size or density of the pattern may differ between portions. Seventh fracture plate 368 preferably includes several portions disposed along lower surface 369. In particular, seventh fracture plate 368 preferably includes first portion 370, second portion 372, and third portion 374. In some embodiments, each of these portions 370, 372 and 374 may include a bone growth promoting agent disposed in a geometric pattern. In a preferred embodiment, first portion 370 and third portion 374 may include a first bone growth promoting agent 376 disposed in a high density geometric pattern. Likewise, second portion 372 may include a second bone growth promoting agent 378 disposed in a low density geometric pattern.

In the previous embodiments, a bone growth promoting agent was applied along portions that were disposed along the width of the fracture plates. In some embodiments, however, the bone growth promoting agent may be disposed along portions that are oriented along the length of the fracture plates. Additionally, a fracture plate may be divided into several portions disposed along the length of the fracture plate, each portion including a different type of bone growth promoting agent.

Figure 40:
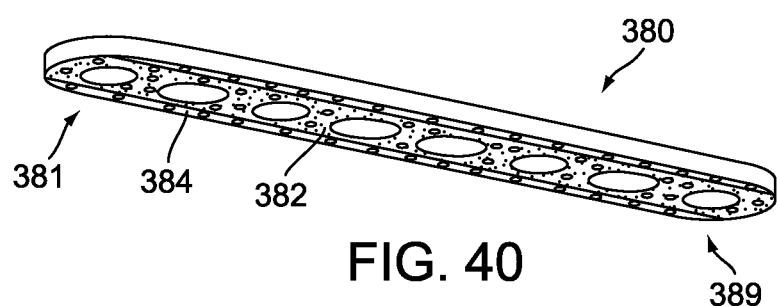
FIG. 40 is an isometric view of a preferred embodiment of a fracture plate with a bone growth promoting agent.
Figure 41:
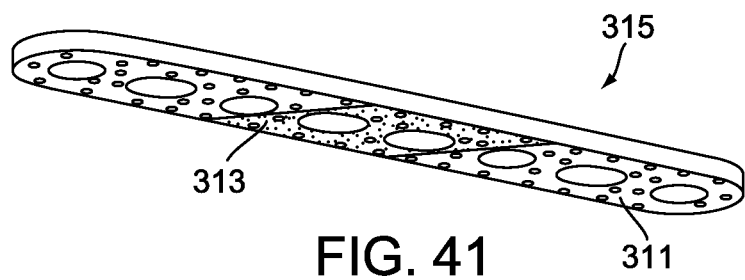
FIG. 41 is an isometric view of a preferred embodiment of a fracture plate with a bone growth promoting agent.

FIG. 40 is a preferred embodiment of fracture plate 380. In some embodiments, fracture plate 380 may include lower surface 381. In some embodiments, lower surface 381 may be coated with bone growth promoting agent 382 along vertical portion 389. FIG. 41 illustrates an embodiment of a fracture plate. In this embodiment, fracture plate 315 includes a diagonally applied bone growth promoting agent 313 onto lower surface 311. Using either a vertically or diagonally applied bone growth promoting agent may facilitate new bone growth along the length of a fracture plate.

In some embodiments, a fracture plate may include additional provisions for inducing bone growth, such as a porous surface. Additionally, fracture plate 380 may include holes 384 disposed along lower surface 381. Generally, holes 384 may have circumferences of various sizes. Likewise, holes 384 may have various depths. Holes 384 need not be disposed along the entirety of fracture plate 380. In some embodiments, holes 384 may be confined to one or multiple portions of a fracture plate. As disclosed above, fracture plate 380 is an example of a prosthesis that includes both macroscopic holes 384 and microscopic bone growth promoting features or agents 382. These macroscopic and microscopic features can be used in combination to help integrate fracture plate 380 to the bone in a macroscopic and microscopic scale.

In another embodiment, a fracture plate may include a liner. In some embodiments, the liner may fit into a recess disposed in the fracture plate. However, in other embodiments, no recess is provided for the liner. Generally, the liner may be formed of or coated with a bone growth promoting agent. The bone growth promoting agent may be disposed on the liner in any pattern, such as those patterns described above with respect to the fracture plate. In this manner, a liner with a bone growth promoting agent may be manufactured separately from the fracture plate, and combined with the fracture plate at the time of surgery, during implantation, or after implantation. It is also possible to provide a fracture plate with a pre-installed liner so there is no need for the surgeon to associate the liner with the fracture plate at the time of surgery.

In some embodiments, the liner may be attached to the fracture plate through an adhesive. It is also possible to attach the liner to the fracture plate by using mechanical provisions, including hooks, microscopic hooks, temperature difference, interference fit, or a Morris taper. It is also possible to attach the liner to the fracture plate using magnetic features. In some embodiments, liner may be preconfigured to include an adhesive for attaching to the fracture plate.

Figure 42:
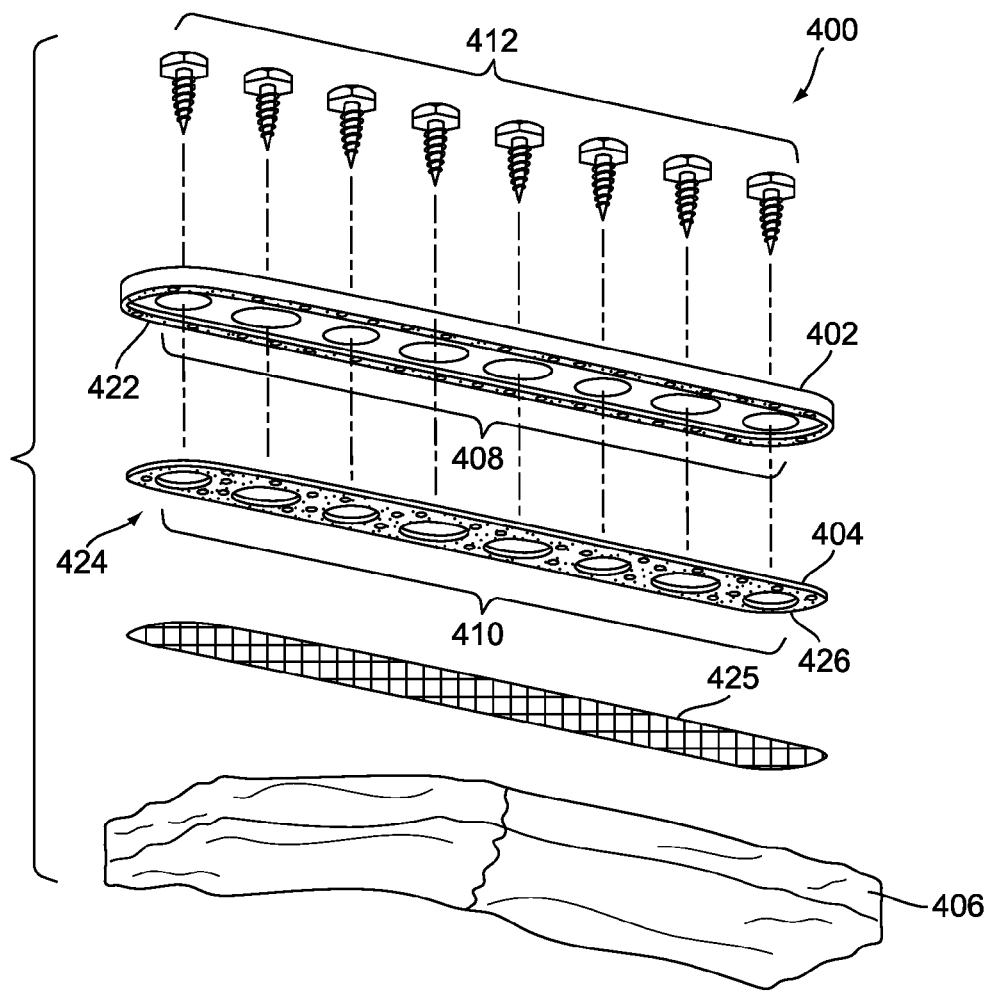
FIG. 42 is an isometric view of a preferred embodiment of a liner system.

FIG. 42 is an exploded view of a preferred embodiment of liner system 400. Liner system 400 preferably includes fracture plate 402. Preferably, fracture plate 402 includes lower surface 422. In some embodiments, recess 420 may be disposed along lower surface 422 of fracture plate 402. Recess 420 may include second set of holes 408.

Additionally, liner system 400 also preferably includes liner 404. Liner 404 may be made of a similar material to fracture plate 402. In some embodiments, liner 404 may be a wafer of bone. Using a wafer of bone may help facilitate bone to bone fusion. In some embodiments, liner 404 may include lower surface 424. Preferably, lower surface 424 includes bone growth promoting agent 426. In a preferred embodiment, lower surface 424 is disposed adjacent to bone 406. Liner 404 also preferably includes first set of holes 410.

In some embodiments, liner system 400 may also include mesh 425. Generally, mesh 425 may be treated with a bone growth promoting agent. In some embodiments, mesh 425 may be disposed between liner 404 and bone 406. In other embodiments, liner system 400 may include only mesh 425 or liner 404. In some embodiments, mesh 425 may be a bone wafer, composite, bio-compatible material or a second liner.

In some embodiments, fracture plate 402 may be constructed of a bio-absorbable material. In this manner, fracture plate 402 may eventually dissolve into the tissue surrounding it. This is a preferred situation over situations in which the fracture plate would need to be removed via surgery. In a similar manner, the fracture plate 402, the liner 404 and/or the mesh 425 may be constructed of a bio-absorbable material. Liner 404 and/or mesh 425 can be constructed of bone, collagen, or other biological or bio-compatible materials. In some cases, a bone wafer may be used. Additional liners and/or meshes may be used, resulting in more than two liners and possibly more than two meshes.

Generally, recess 420 may be configured to receive liner 404. In some embodiments, recess 420 has a depth that is equivalent to the thickness of liner 404. In other embodiments, the thickness of liner 404 and the depth of recess 420 may be varied.

Preferably, liner system 400 also includes screw set 412. In some embodiments, second set of holes 408 are configured to receive screw set 412. Generally, first set of holes 410 and second set of holes 408 may be aligned.

Once assembled, liner system 400 may be configured to add support to bone 406. In particular, as liner 404 preferably includes selectively applied bone growth promoting agent 426 along lower surface 424, this may help stimulate the growth of bone 406. Generally, a liner may also include various bone growth promoting agents that may be selectively applied to various regions. The types of bone growth promoting agents and the methods of selectively applying them may be substantially similar to the previous embodiments.

In some embodiments, a fracture plate with holes may help induce bone growth that allows bone to grow into the holes. In this manner, the bone may be partially fused to the fracture plate. Preferably, the plate may include an additional bone growth promoting agent to help stimulate bone growth.

Figure 43:
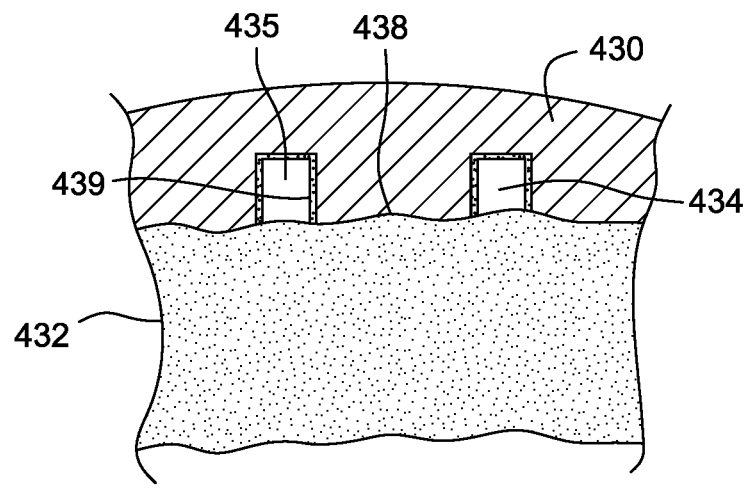
FIG. 43 is a side cross sectional view of a preferred embodiment of a fracture plate contacting a bone.
Figure 44:
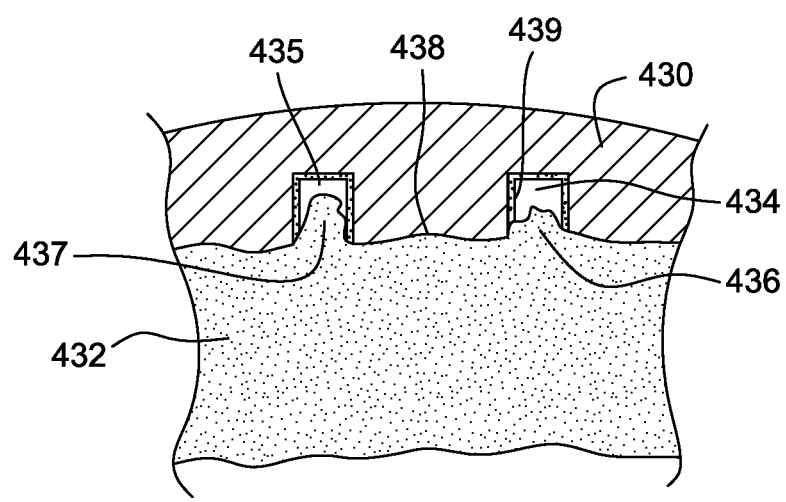
FIG. 44 is a side cross sectional view of a preferred embodiment of a fracture plate with bony fusion.

Referring to FIGS. 43-44, fracture plate 430 may preferably be configured to promote bone growth on the walls of first hole 434, second hole 435, and lower surface 438. This may be achieved with or without the use of a bone growth promoting agent. In a preferred embodiment, bone growth promoting agent 439 may be applied to holes 434 and 435. Generally, fracture plate 430 may be secured to bone 432 by some means, such as a screw. Over time, first portion 436 and second portion 437 of bone 432 may grow into first hole 434 and second hole 435. In addition, bone growth will also occur into the surfaces of first hole 434 and second hole 435. In other words, bone growth can occur on a macroscopic scale—bone growth into holes 434 and 435—and on a microscopic scale as well, bone growth onto the surfaces of holes 434 and 435 due to the bone growth promoting agent applied to the walls of holes 434 and 435.

In an alternative embodiment, the implantable prosthesis may take the form of a screw. In some cases, a screw may be configured to attach multiple bones together. In other cases, a screw may be configured to attach a rod or a fracture plate to a fractured single bone. Generally, a screw may be used with many different kinds of implantable prostheses.

In a manner similar to the rods and fracture plates discussed in the previous embodiments, a bone growth promoting agent may be selectively applied to a screw to stimulate bone growth. Because a screw has a similar structure to a rod, it follows that all of the various modifications that may be made to a rod to include selectively applied bone growth promoting agents may also be applied to the screw disclosed here. In particular, any of the bone growth agents previously disclosed may be applied to any portion of a screw. Also, these bone growth agents may be applied in the patterns disclosed in the previous embodiments.

The term screw as used here applied to any device with threading. In some cases, screws may or may not include a head. Screws can also include a solid or hollow boring tip. This solid boring tip allows the screw to be inserted into a region of bone where no previous hole has been made. Additionally, the head may be associated with a fastening tool, such as a screw driver, hex key or a drill, allowing the screw to be turned.

Figure 45:
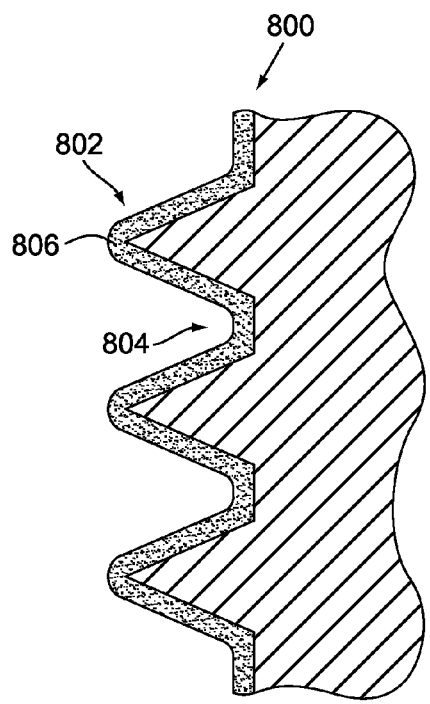
FIG. 45 is a schematic cross section of a preferred embodiment of the threading of a screw.

In FIG. 45, bone growth promoting agent 806 has been applied to threading peaks 802 of threading 800 as well as threading valleys 804 of threading 800. This coating of the entirety of threading 800 may be accomplished by dipping threading 800 in a chemical including bone growth promoting agent 806. The coating can also be applied by spraying, sintering, wax covering, as well as other suitable methods.

Figure 46:
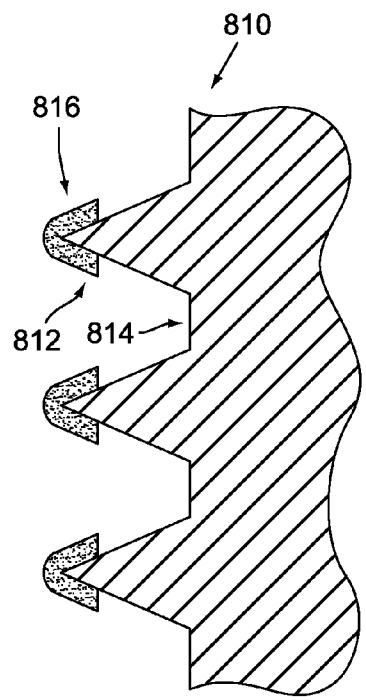
FIG. 46 is a schematic cross section of a preferred embodiment of the threading of a screw.

Additionally, it may be desirable in some cases to only coat a portion of the threading. This can provide different degrees of incorporation into the bone. In some cases, limited degrees of incorporation may be helpful to assist in later removal of the screw. Referring to FIG. 46, it may be possible to only apply bone growth promoting agent 816 to threading peaks 812 of threading 810. In this manner, threading valleys 814 may not include bone growth promoting agent 816. This feature may be accomplished by quickly dipping threading 810 into a chemical including bone growth promoting agent 816 before the chemical has time to fill into thread valleys 814. Additionally, the coating can also be applied by spraying, sintering, wax covering, as well as other suitable methods.

Figure 47:
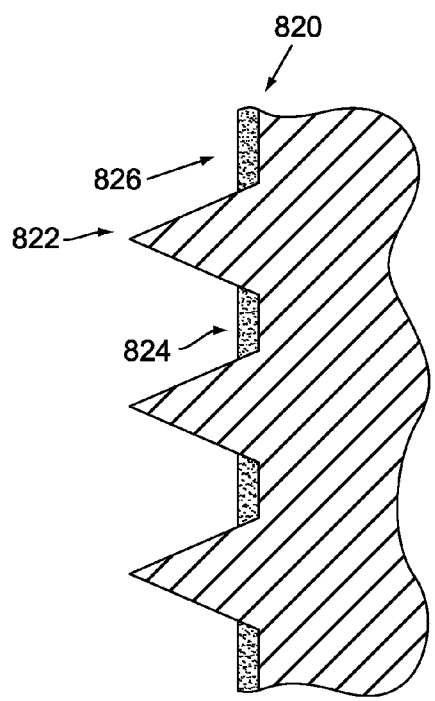
FIG. 47 is a schematic cross section of a preferred embodiment of the threading of a screw.

In some cases, only the threading valleys may be coated. Referring to FIG. 47, threading valleys 824 of threading 820 may be coated with bone growth promoting agent 826. This may be accomplished by dipping threading 820 into a chemical including bone growth promoting agent 826, and then spinning the screw in a manner that expels the bone growth promoting agent 826 from threading peaks 822. Additionally, the coating can also be applied by spraying, sintering, wax covering, as well as other suitable methods.

Figure 48:
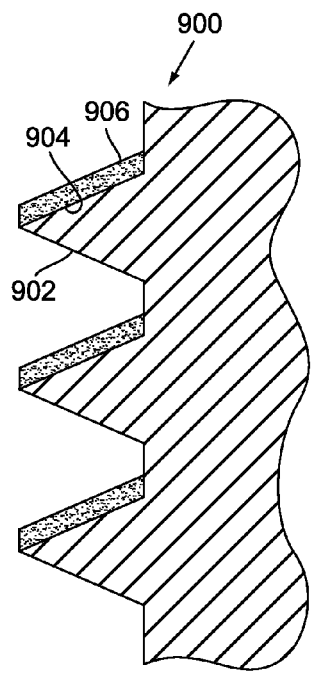
FIG. 48 is a schematic cross section of a preferred embodiment of the threading of a screw.
Figure 49:
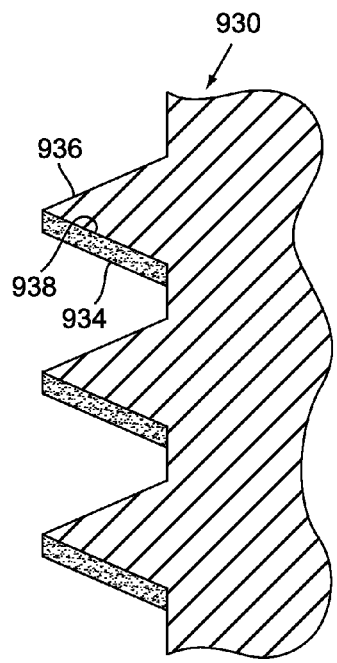
FIG. 49 is a schematic cross section of a preferred embodiment of the threading of a screw.
Figure 50:
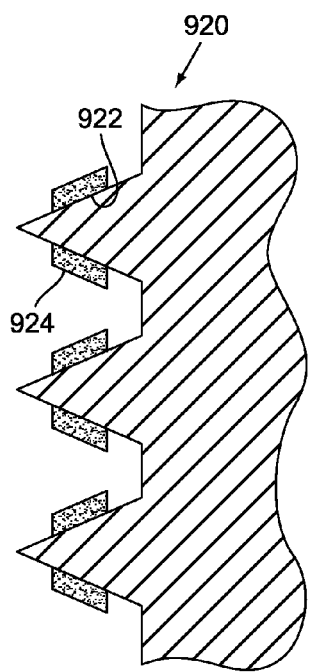
FIG. 50 is a schematic cross section of a preferred embodiment of the threading of a screw.
Figure 51:
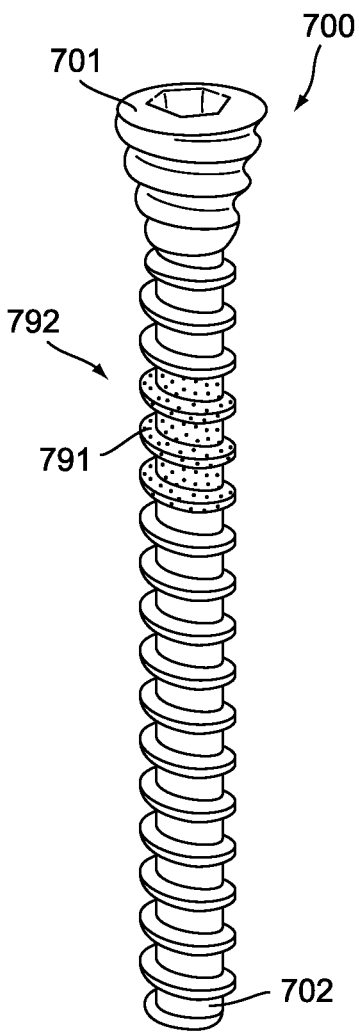
FIG. 51 is a side view of a preferred embodiment of a screw.
Figure 52:
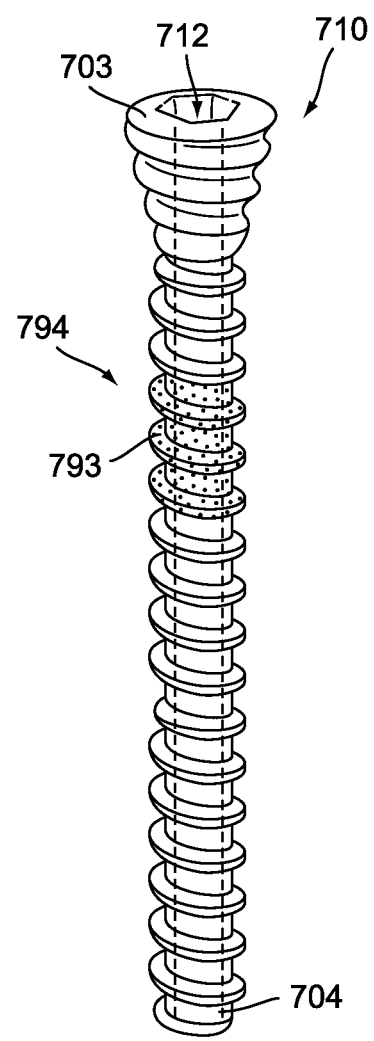
FIG. 52 is a side view of a preferred embodiment of a screw.
Figure 53:
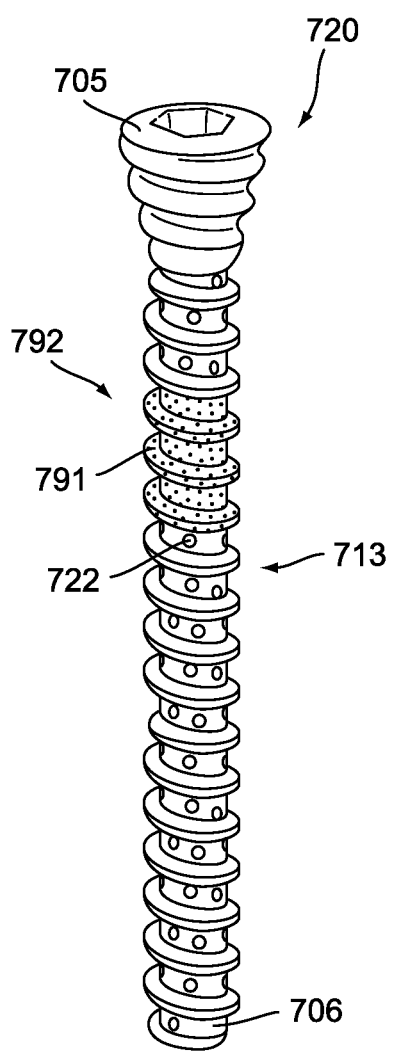
FIG. 53 is a side view of a preferred embodiment of a screw.
Figure 54:
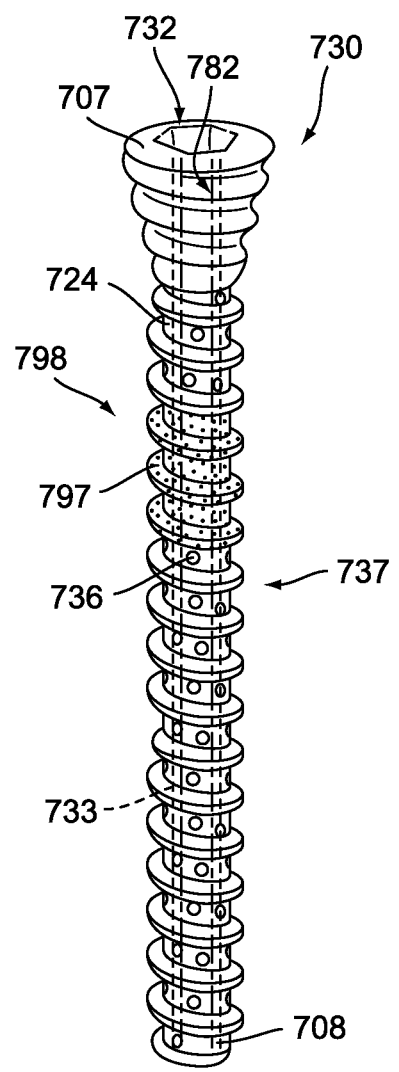
FIG. 54 is a side view of a preferred embodiment of a screw.

In other embodiments, only portions of the threading may be coated. Referring to FIG. 48, threading 900 preferably includes upper portions 904 and lower portions 902. In this embodiment, only upper portions 904 of threading 900 may be coated with bone growth promoting agent 906. Likewise, in the embodiment shown in FIG. 49, threading 930 may include upper portions 936 and lower portions 938. In this embodiment, only lower portions 938 of threading 930 may be coated with bone growth promoting agent 934. Finally, in the embodiment shown in FIG. 50, only middle portions 922 of threading 920 may be coated with bone growth promoting agent 924. As with the previous embodiments, each of the coatings may be applied using techniques such as spraying, sintering, wax covering, as well as other suitable techniques.

In some embodiments, the structure of a screw may be modified. Such modifications include hollowing out the screw, as well as adding holes to the screw. Generally, a screw may be modified in ways similar to the rods disclosed above. The screws may be fully, partially or non-cannulated screws and the coatings may be applied in whole or in part in a manner similar to the coatings applied to the rods as disclosed above.

Referring to FIGS. 51-54, screws may be configured solid, hollow, and with or without holes. One example of a hollow screw is a cannulated screw, which includes a hollow central shaft. In one embodiment, a section of screw 700 may be solid. Screw 700 also preferably includes screw head 701 and boring tip 702. In some embodiments, bone growth promoting agent 791 may be applied to first region 792. Preferably, bone growth promoting agent 791 is only applied to first region 792 and not the entire shaft of screw 700. Likewise, throughout the remaining embodiments seen in FIGS. 52-54, bone growth promoting agents have been applied only to a selected region of the screw, not to the entirety. In this manner, screw 700 may stimulate bone growth along portions of a bone disposed adjacent to first region 792.

In a second embodiment, screw 710 may include hollow central core 712. Second screw 710 may include screw head 703 and boring tip 704. In some embodiments, bone growth promoting agent 793 may be applied to first region 794. In this manner, screw 710 may stimulate bone growth along portions of a bone disposed adjacent to first region 794.

Preferably, in a third embodiment, screw 720 may include holes 722. Holes 722 are preferably disposed along a first portion 713 of screw 720. Generally, holes 722 may be any depth, any shape, angle, and have any size circumference. Similarly, the density of holes 722 may be varied in other embodiments. In some embodiments, a combination of holes having different sizes, shapes, angles, or densities may be used. Preferably, screw 720 may also include screw head 705 and boring tip 706. In some embodiments, bone growth promoting agent 795 may be applied to second portion 796. In this manner, screw 720 may stimulate bone growth along portions of a bone disposed adjacent to first region 796. In a preferred embodiment, a bone growth promoting agent is not applied to screw head 705.

A fourth embodiment of a section of screw 730 may preferably include hollow central core 732 as well as holes 736. Holes 736 are preferably disposed along first portion 737 of screw 730. Generally, holes 736 may be any depth, any shape, angle, and have any size circumference. Similarly, the density of holes 736 may be varied in other embodiments. In some embodiments, a combination of holes having different sizes, shapes, angles, or densities may be used. In a preferred embodiment, holes 736 may be disposed between outer surface 729 and inner surface 733 of hollow central core 732. In this manner, holes 736 preferably allow fluid communication between hollow central core 732 and outer surface 729. Preferably, fourth screw 730 may also include screw head 707 and boring tip 708. In some embodiments, bone growth promoting agent 797 may be applied to first region 798. In this manner, screw 730 may stimulate bone growth along portions of a bone disposed adjacent to first region 798. In a preferred embodiment, inner surface 733 may include bone growth promoting agent 782 as well. Bone growth promoting agent 782 applied to inner surface 733 may be similar or different than bone growth promoting agent 797 that is applied to first region 798. The various bone growth promoting agents can be selected to achieve different bone growth properties and/or to encourage different rates or kinds of bone growth. In a preferred embodiment, a bone growth promoting agent is not applied to screw head 707.

Generally, the length of the central cavities 712 and 732 of the previous embodiments may be varied. Preferably, central cavities 712 and 732 extend all the way to the bottom of screws 710 and 730. Instead, the end of screws 710 and 730 are preferably solid, as is preferable for boring into bone. Additionally, the tops of screws 710 and 730 need not be configured open. In some embodiments, the tops of screws 710 and 730 may be configured closed. Furthermore, screw heads in any embodiment may include features to mate with any desired driver. For example, the screw heads may include a slot, Phillips, star, hexagonal cavity, torx, hexagonal nut or any other desired mechanical coupling. In other embodiments, the screw does not have a head, and the shaft includes features to mate with any desired driver.

Figure 55:
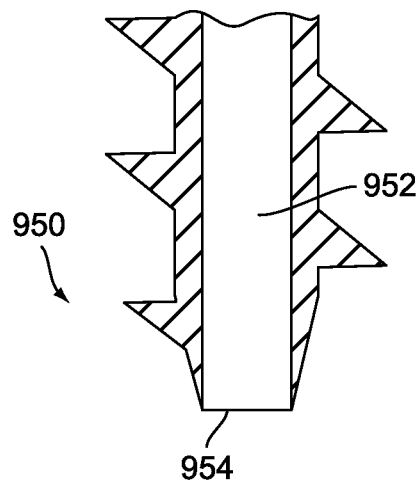
FIG. 55 is a close up cross sectional view of a screw with a hollow boring tip.
Figure 56:
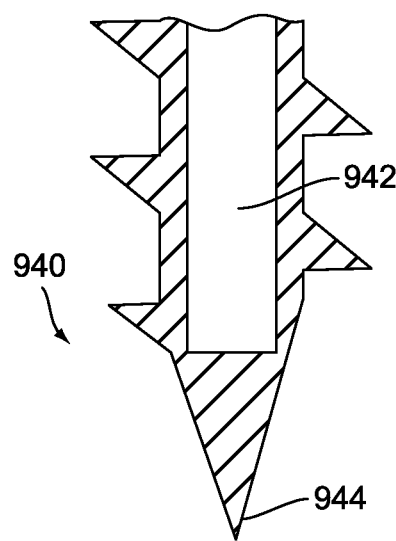
FIG. 56 is a close up cross sectional view of a screw with a solid boring tip.

Additionally, in some embodiments, the tips of the screws including bone growth promoting agents may be configured as open or closed. In other words, the tips may have a hollow or solid boring tip. Referring to FIG. 55, a screw including tip portion 950 includes central cavity 952 that extends all the way through boring tip 954. In another embodiment, seen in FIG. 56, a screw including tip portion 940 includes central cavity 942 with a solid boring tip 944.

In a manner similar to the rods and cages of the previous embodiments, a screw may be configured to promote ingrowth of bone and fuse with the bone. In some embodiments, a screw including holes and a hollow central core may be implanted into a bone. Once the screw has been implanted inside the bone, growth may occur through the holes into the hollow central core. In a preferred embodiment, the outer and inner surfaces of the screw may be coated with a bone growth promoting agent.

Figure 57:
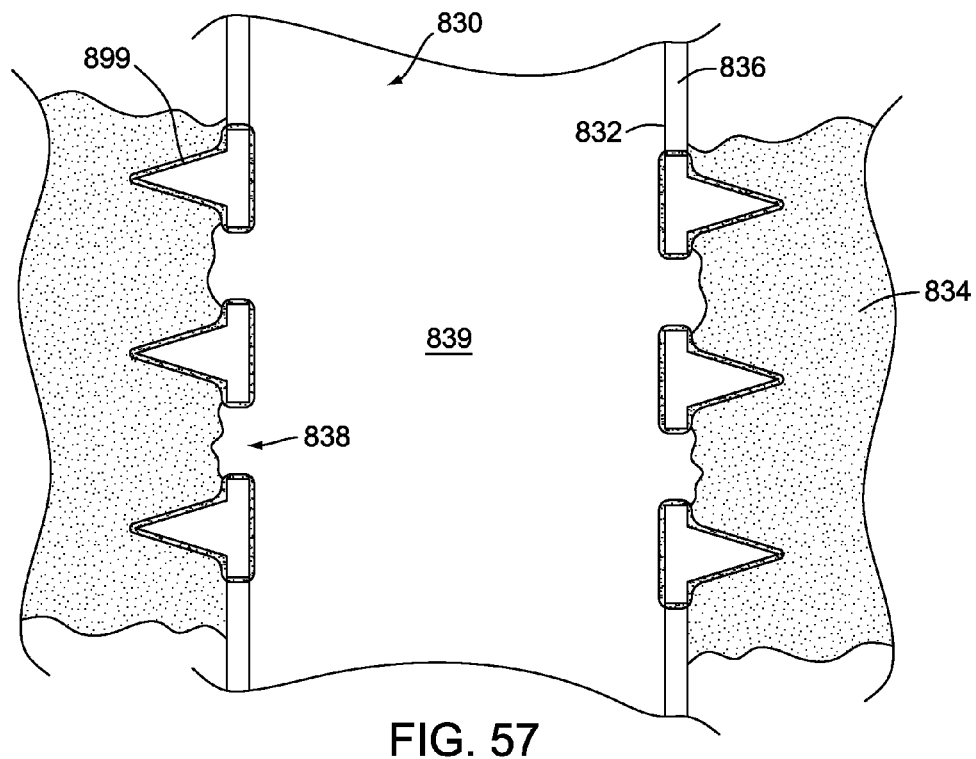
FIG. 57 is a schematic cross section of a preferred embodiment of a screw inserted into bone.
Figure 58:
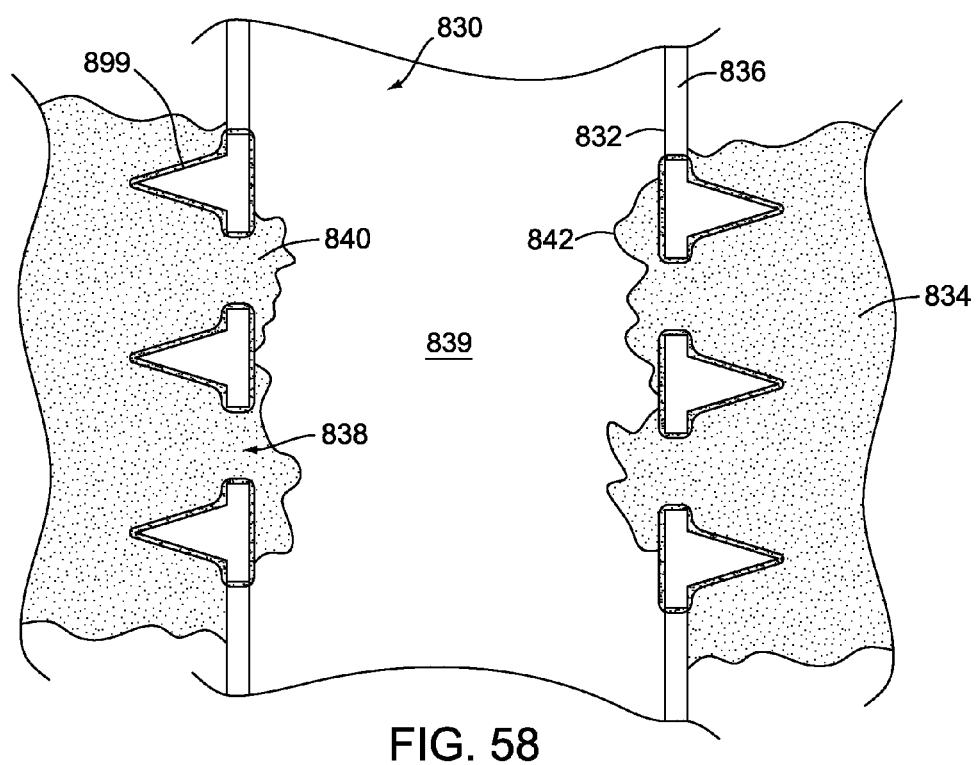
FIG. 58 is a schematic cross section of a preferred embodiment of bone growing into a hollow central core of a screw.

Referring to FIGS. 57-58, ingrowth of the bone from outer surface 836 to inner surface 832 may proceed once screw 830 has been inserted into a section of bone 834. With time, portions 840 of bone 834 may grow through holes 838 into hollow central core 839. In some embodiments, portions 840 may fuse together within hollow central core 839. In this way, screw 830 may be fused with bone 834. In a preferred embodiment, holes 838 are used in conjunction with bone growth promoting agent 899 disposed along inner surface 832 and outer surface 836 in order to induce bone growth. In some embodiments, bone growth promoting agent 899 may also be disposed within holes 838. In this manner, screw 830 may be partially or fully integrated into bone 834 as it is healing, micro and macroscopically.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. An implantable prosthesis system, comprising:
    a fracture plate configured to be attached to a bone;
    the fracture plate including a first portion and a second portion along a lower surface;
    wherein a bone growth promoting agent is selectively applied to the first portion of the lower surface;
    wherein the second portion lacks the bone growth promoting agent;
    wherein the fracture plate includes a third portion;

wherein the second and third portions are separated by the first portion;
wherein the bone growth promoting agent is disposed in one of a vertical strip and a diagonal strip in the first portion; and
wherein the second and third portions lack the bone growth promoting agent.

2. The implantable prosthesis system according to claim 1, wherein the fracture plate includes holes.

3. The implantable prosthesis system according to claim 2, wherein each hole extends partially into the lower surface.

4. The implantable prosthesis system according to claim 3, wherein each hole includes a bone growth promoting agent applied to at least one of a side wall surface and a distal wall surface of the each hole.

5. The implantable prosthesis system according to claim 2, wherein the holes are configured to contact a tissue adjacent to the bone.

6. The implantable prosthesis system according to claim 1, wherein the fracture plate includes at least one hole configured to receive a screw.

7. The implantable prosthesis system according to claim 6, wherein the fracture plate includes two holes, each hole being configured to receive a screw.

8. The implantable prosthesis system according to claim 6, wherein the fracture plate includes more than two holes.

9. An implantable prosthesis system, comprising:
a fracture plate configured to be attached to a bone;
the fracture plate including a recess;
a liner disposed within the recess, wherein the liner includes a first portion and a second portion along a lower surface configured to contact the bone;
wherein a bone growth promoting agent is selectively applied to the first portion of the lower surface;
wherein the liner includes a third portion along the lower surface;
wherein the second and third portions are separated by the first portion;
wherein a bone growth promoting agent is disposed in a first design on the first portion;
wherein a bone growth promoting agent is disposed in a second design on the second portion of the lower surface; and
wherein the first design is different from the second design.

10. The implantable prosthesis system according to claim 9, wherein the depth of the recess is approximately equal to the thickness of the liner.

11. The implantable prosthesis system according to claim 9, wherein the liner is a wafer of bone.

12. The implantable prosthesis system according to claim 9, wherein the liner is attached to the fracture plate with an attachment selected from the group consisting essentially of an adhesive, hooks, microscopic hooks, temperature difference, interference fit, a Morris taper, and magnetic features.

13. An implantable prosthesis system comprising:
a fracture plate configured to be attached to a bone;
the fracture plate including a recess;
a liner disposed within the recess, wherein the liner includes a first portion and a second portion along a lower surface configured to contact the bone;
wherein a bone growth promoting agent is selectively applied to the first portion of the lower surface;
wherein the liner includes a third portion;
wherein the second and third portions are separated by the first portion;
wherein the bone growth promoting agent is disposed in one of a vertical strip and a diagonal strip in the first portion; and
wherein the second and third portions lack the bone growth promoting agent.

14. The implantable prosthesis system according to claim 13, wherein the fracture plate includes a plurality of holes each extending partially into the lower surface.

15. The implantable prosthesis system according to claim 9, wherein the liner includes a plurality of holes each extending partially into the lower surface.

16. The implantable prosthesis system according to claim 9, wherein a bone growth promoting agent is disposed in the second design on the third portion.

17. An implantable prosthesis system, comprising:
a fracture plate configured to be attached to a bone;
the fracture plate including a first portion, a second portion, and a third portion along a lower surface;
wherein the first and third portions are separated by the second portion;
wherein a bone growth promoting agent is disposed in a first design on the first portion of the lower surface;
wherein a bone growth promoting agent is disposed in a second design on the second portion of the lower surface; and
wherein the first design is different from the second design.

18. The implantable prosthesis system according to claim 17, wherein a bone growth promoting agent is disposed in the first design on the third portion of the lower surface.

19. The implantable prosthesis system according to claim 18, wherein the first design comprises a striped pattern and the second design comprises a spotted pattern.

20. The implantable prosthesis system according to claim 18, wherein the first design comprises a high density geometric pattern and the second design comprises a low density geometric pattern.

21. An implantable prosthesis system comprising:
a fracture plate configured to be attached to a bone;
the fracture plate including a recess;
a liner disposed within the recess, wherein the liner includes a first portion and a second portion along a lower surface configured to contact the bone;
wherein a bone growth promoting agent is selectively applied to the first portion of the lower surface;
wherein the liner includes a third portion along the lower surface;
wherein the second and third portions are separated by the first portion;
wherein the bone growth promoting agent is disposed in one of a striped pattern, a spotted pattern, and a geometric pattern in the first portion; and
wherein the second and third portions lack the bone growth promoting agent.

* * * * *